(12) United States Patent
Moore et al.

(10) Patent No.: US 11,849,973 B2
(45) Date of Patent: Dec. 26, 2023

(54) IMPLANT REMOVAL DEVICES AND METHODS

(71) Applicants: Russell David Moore, St Paul, MN (US); Choon Hyong Lee, Irvine, CA (US)

(72) Inventors: Russell David Moore, St Paul, MN (US); Choon Hyong Lee, Irvine, CA (US)

(73) Assignee: Russell David Moore, Jersey City, NJ (US)

( * ) Notice: Subject to any disclaimer, the term of this patent is extended or adjusted under 35 U.S.C. 154(b) by 217 days.

(21) Appl. No.: 17/229,968

(22) Filed: Apr. 14, 2021

(65) Prior Publication Data
US 2021/0322056 A1    Oct. 21, 2021

Related U.S. Application Data

(60) Provisional application No. 63/010,758, filed on Apr. 16, 2020.

(51) Int. Cl.
*A61B 17/50* (2006.01)
*A61B 17/30* (2006.01)
(Continued)

(52) U.S. Cl.
CPC ........ *A61B 17/50* (2013.01); *A61B 17/32093* (2013.01); *A61B 17/00* (2013.01);
(Continued)

(58) Field of Classification Search
CPC ... A61B 17/50; A61B 17/3468; A61B 17/285; A61B 17/22031; A61B 2017/305; A61B 2017/505; A61B 17/30; A61B 17/32093; A61B 2017/00353; A61B 2017/00747; A61B 17/00; A61B 2017/320064
(Continued)

(56) References Cited

U.S. PATENT DOCUMENTS 5,064,429 A * 11/1991 Waterman .......... A61B 17/1227
606/151
5,242,453 A    9/1993 Gubich
(Continued)

OTHER PUBLICATIONS

International Patent Application No. PCT/US2021/027184, International Search Report and Written Opinion dated Aug. 4, 2021, 14 pg.

*Primary Examiner* — Timothy J Neal
*Assistant Examiner* — Mitchell Brian Hoag
(74) *Attorney, Agent, or Firm* — Fredrikson & Byron, P.A.

(57) ABSTRACT

An implant removal device includes a body, a first arm, a second arm, an actuation interface, and an extraction member. The first arm is supported at the body and configured to move relative to the body between a retracted position and a skin gripping position. The second arm is supported at the body and configured to move relative to the body between the retracted position and the skin gripping position. The actuation interface is supported at the body. The actuation interface is configured to receive a first actuation input thereat to cause at least one of the first arm and the second arm to move from the skin gripping position to the retracted position. The extraction member is supported at the body and located between the first arm and the second arm.

20 Claims, 14 Drawing Sheets

(51) Int. Cl.
*A61B 17/285* (2006.01)
*A61B 17/3209* (2006.01)
*A61B 17/00* (2006.01)
*A61B 17/32* (2006.01)

(52) U.S. Cl.
CPC ............ *A61B 17/285* (2013.01); *A61B 17/30* (2013.01); *A61B 2017/00353* (2013.01); *A61B 2017/00747* (2013.01); *A61B 2017/305* (2013.01); *A61B 2017/320064* (2013.01); *A61B 2017/505* (2013.01)

(58) Field of Classification Search
USPC ........................................................ 606/131
See application file for complete search history.

(56) References Cited

U.S. PATENT DOCUMENTS

| | | | |
|---|---|---|---|
| 10,314,617 | B2 | 6/2019 | Bratlie |
| 2005/0149064 | A1* | 7/2005 | Peterson ............... A61B 17/068 606/143 |
| 2013/0211440 | A1* | 8/2013 | Schwab ................. A61F 5/003 606/192 |
| 2014/0046125 | A1* | 2/2014 | Gillespie, Jr. ...... A61B 17/3478 600/31 |
| 2016/0166277 | A1* | 6/2016 | Suwito ............... A61B 17/3468 606/167 |
| 2016/0354115 | A1 | 12/2016 | Smith et al. |
| 2018/0168673 | A1* | 6/2018 | Bratlie ............. A61B 17/32093 |
| 2019/0125376 | A1* | 5/2019 | Batchelor ............ A61B 90/03 |
| 2019/0274731 | A1 | 9/2019 | Bratlie |
| 2020/0078035 | A1 | 3/2020 | Britland |
| 2020/0121342 | A1* | 4/2020 | Sullivan, III ...... A61B 17/2909 |

* cited by examiner

IMPLANT REMOVAL DEVICES AND METHODS

RELATED APPLICATION

This application claims the benefit of U.S. provisional patent application No. 63/010,758, filed on Apr. 16, 2020.

TECHNICAL FIELD

This disclosure relates generally to implant removal devices and related methods of using an implant removal device to remove an implant. In particular, embodiments are described herein in the context of subdermal implant removal devices and methods.

BACKGROUND

Implants are used for a variety of medical purposes at various anatomical locations. For instance, certain types of implants are positioned underneath the skin and referred to as subdermal implants. One common type of subdermal implant is a long-term contraceptive. This long-term contraceptive is generally in the form of a rod and implanted underneath the skin of a patient where it releases one or more contraceptive hormones, such as a synthetic progestin etonogestrel, for a period of time. Because the contraceptive subdermal implant is non-biodegradable, it must be removed once the one or more contraceptive hormones it carries are depleted. In general, contraceptive subdermal implants are removed and replaced every two to three years, depending on the particular type of contraceptive implant.

However, current techniques for removing subdermal implants, including generally rod form contraceptive subdermal implants, are time-consuming and tedious for the clinician and uncomfortable, oftentimes even painful, for the patient. Subdermal implants are generally removed in an ad hoc, manual manner, and there is no standardized removal technique. In general, these current techniques involve the clinician using one hand to variably manipulate the skin around the subdermal implant while using the other hand to attempt to align the subdermal implant with an incision at the skin and force the subdermal implant out from underneath the skin through the incision. As such, this process entails a significant amount of trial and error. Given the imprecise nature of the current manual, ad hoc technique for removing a subdermal implant, it oftentimes can take several cycles of this hands-on process to ultimately remove the implant from underneath the patient's skin.

SUMMARY

In general, various embodiments relating to implant removal devices and related methods are disclosed herein. In particular, the implant removal device and method embodiments disclosed herein can be especially useful as subdermal implant removal devices and methods. These embodiments can facilitate efficient removal of a subdermal implant in a manner that can reduce clinician time and effort and decrease patient discomfort. Moreover, these embodiments can provide this efficient subdermal implant removal solution in a manner that is repeatable across varying anatomical characteristics from patient-to-patient and, thus, provide a more standardized subdermal implant removal solution. These embodiments can accomplish such advantages by optimizing the application of force at the skin surface around the subdermal implant and increasing the precision of implant alignment with, and removal through, an incision at the skin.

One embodiment includes an implant removal device. This implant removal device embodiment includes a body, a first arm, a second arm, and an extraction member. The first arm and the second arm are each supported at the body and movable relative to the body between a retracted position and a skin gripping position. When moved, relative to the body, to the skin gripping position, the first and second arms are configured to contact and raise respective skin surfaces on opposite sides of an implant. The extraction member is supported at the body and movable relative to the body between an implant engagement position and an implant removal position. As the extraction member is moved, relative to the body, from the implant engagement position toward the implant removal position, the extraction member is configured to urge the implant toward an incision at a skin surface.

In this embodiment, the implant removal device can be configured to reduce the likelihood of implant breakage during removal by supporting the implant along at least a majority (e.g., all) of its longitudinal axis. Current techniques for removing a subdermal implant, such as that described in the Background, can cause the implant to break before it is removed from underneath the skin surface. This can result because these current techniques apply relatively high localized pressure at particular portions of the implant. In the case of an elongated rod subdermal implant, these current techniques may apply relatively high localized pressure at a smaller region along the implant's longitudinal axis (e.g., via a clinician's fingers pinching the road on both sides). Embodiments of the implant removal device embodiment disclosed herein can reduce the likelihood that the implant breaks during removal by distributing forces along at least a majority (e.g., all) of the implant's longitudinal axis. For example, the implant removal device can include two arms each configured to apply a force at the skin surface along a length equal to at least at least a majority (e.g., all) of a length of the implant as measured along its longitudinal axis. In this way, the arms of the implant removal device can support the implant along its longitudinal axis at locations adjacent along each lateral side of the implant and thereby can reduce the likelihood that the implant breaks during the removal process.

A further embodiment of the implant removal device includes a first button and a second button. Each of the first button and the second button is located at the body. When a first actuation input applied at the first button, the first button is configured to move the first arm from the retracted position to the skin gripping position. And, when the first actuation input is applied at the second button, the second button is configured to move the second arm from the retracted position to the skin gripping position. When a second actuation input is applied at the first button and/or the second button, the first button and/or the second button is configured to move the extraction member from the implant engagement position toward the implant removal position. In one example, the extraction member can move between the first and second arms toward the implant removal position.

In another further embodiment, the implant removal device additionally includes a guide slot and a force imparting interface. The guide slot and the force imparting interface are each defined at the body. Each of the guide slot and the force imparting interface can be located on a common radial axis of the implant removal device (e.g., the radial axis being perpendicular to a longitudinal axis of the implant removal device, such as the radial axis being perpendicular to an axis along which the extraction member moves between the implant engagement position and the implant removal position). The force imparting interface can be configured to contact a skin surface, such as a skin surface interfacing with an end of the incision. When a force is applied at a handle on the body, the force imparting interface can be configured to push this skin surface downward and, thereby, align at least a portion of the incision with the guide slot. In this way, the force imparting interface can help to remove the implant through the incision and out from the implant removal device through the guide slot.

Another embodiment includes a method of removing a subdermal implant. This method embodiment includes positioning an implant removal device at a skin surface. Once the implant removal device is positioned at the skin surface, one or more arms of the implant removal device are moved, relative to a body of the implant removal device, to a skin gripping position. When moved to the skin gripping position, the one or more arms are configured to contact and raise respective skin surfaces on opposite sides of an implant that is located beneath the skin surface. The method also includes moving an extraction member of the implant removal device along the skin surface. For example, the extraction member can be moved along the skin surface from an implant engagement position to an implant removal position. The extraction member can be moved as such while the one or more arms are at the skin gripping position. The method can further include removing the implant through an incision at the skin surface. For example, a force can be applied to a force imparting interface of the implant removal device to cause the force imparting interface to align the incision with a guide slot defined at the implant removal device. Then, as the extraction member is moved along the skin surface from the implant engagement position toward the implant removal position, the implant can be urged, underneath the skin surface, toward the guide slot and ultimately through the incision and out from the guide slot.

Another embodiment of an implant removal device includes a body, a first arm, a second arm, an actuation interface, and an extraction member. The first arm is supported at the body and configured to move relative to the body between a retracted position and a skin gripping position. The second arm is supported at the body and configured to move relative to the body between the retracted position and the skin gripping position. The actuation interface is supported at the body. The actuation interface is configured to receive a first actuation input thereat to cause at least one of the first arm and the second arm to move from the skin gripping position to the retracted position. The extraction member is supported at the body and located between the first arm and the second arm.

In a further embodiment of this implant removal device, as the first arm is moved from the retracted position to the skin gripping position, the first arm can be configured to contact and raise a skin surface at a first side of an implant. And, as the second arm is moved from the retracted position to the skin gripping position, the second arm can be configured to contact and raise the skin surface at a second side of the implant. This second side can be opposite the first side. In some examples, the extraction member can be located between the first arm and the second arm when the first arm and the second arm are in the skin gripping position. And, the extraction member can be configured to engage an end portion of the implant extending between the first side of the implant and the second side of the implant when the first arm and the second arm are in the skin gripping position.

In a further embodiment of this implant removal device, a space defined between the first arm and the second arm is greater when the first arm and the second arm are in the retracted position than when the first arm and the second arm are in the skin gripping position. Also, each of the first arm and the second arm can be biased to the skin gripping position. In some such examples, the body can be configured to impart a biasing force on each of the first arm and the second arm to bias each of the first arm and the second arm to the skin gripping position. The body can be configured such that the biasing force is overcome by application of the first actuation input at the actuation interface to cause each of the first arm and the second arm to move from the skin gripping position to the retracted position. And, the body can be configured such that, upon removal of the first actuation input at the actuation interface, the biasing force moves each of the first arm and the second arm from the retracted position to the skin gripping position.

In a further embodiment of this implant removal device, the actuation interface can include a first handle and a second handle. The first handle can be configured to receive the first actuation input thereat to cause the first arm to move from the skin gripping position to the retracted position, and the second handle can be configured to receive the first actuation input thereat to cause the second arm to move from the skin gripping position to the retracted position. The body can include a biasing member that is configured to impart a biasing force on each of the first arm and the second arm to bias each of the first arm and the second arm to the skin gripping position. The first handle can be supported at a first side of the biasing member, and the second handle can be supported at a second side of the biasing member, where the second side is opposite the first side. As one particular example, the biasing member can include a C-shaped element having a first C-shaped end and a second C-shaped end opposite the first C-shaped end. And, the first handle can be supported at the first C-shaped end, and the second handle can be supported at the second C-shaped end.

In a further embodiment of this implant removal device, the first arm includes a first skin interfacing surface and the second arm includes a second skin interfacing surface. The first skin interfacing surface includes a first skin interfacing surface first convex region at an upper portion of the first arm and a first skin interfacing surface second convex region at a lower portion of the first arm, where the lower portion of the first arm is opposite the upper portion of the first arm. The second skin interfacing surface includes a second skin interfacing surface first convex region at an upper portion of the second arm and a second skin interfacing surface second convex region at a lower portion of the second arm, where the lower portion of the second arm is opposite the upper portion of the second arm. In a further example, the first skin interfacing surface also includes a first skin interfacing surface planar region that interconnects the first skin interfacing surface first convex region and the first skin interfacing surface second convex region, and the second skin interfacing surface also includes a second skin interfacing surface planar region that interconnects the second skin interfacing surface first convex region and the second skin interfacing surface second convex region. The first skin interfacing surface of the first arm and the second skin interfacing surface of the second arm can face toward one another.

In a further embodiment of this implant removal device, the first arm can include a first end portion, opposite the actuation interface, having a first width, defined in a direction normal to a longitudinal axis of the first arm, that increases in a direction moving along the longitudinal axis of the first arm toward the actuation interface. Likewise, the second arm can include a second end portion, opposite the actuation interface, having a second width, defined in a direction normal to a longitudinal axis of the second arm, that increases in a direction moving along the longitudinal axis of the second arm toward the actuation interface. In one specific example, the first end portion can be wedge-shaped and the second end portion can be wedge-shaped.

Another embodiment of a method includes the step of positioning an implant removal device at a skin surface with each of a first arm and a second arm of the implant removal device in a retracted position. This method embodiment also includes the step of moving each of the first arm and the second arm of the implant removal device from the retracted position to a skin gripping position such that the first arm is adjacent a first side of an implant and the second arm is adjacent a second side of the implant. The second side is opposite the first side, and the first arm and the second arm are closer together in the skin gripping position than in the retracted position. This method embodiment further includes the step of moving an extraction member of the implant removal device into engagement with the skin surface adjacent an end portion of the implant. The end portion of the implant extends between the first side of the implant and the second side of the implant. The extraction member is located between the first arm and the second arm. And, this method embodiment includes the step of moving the implant, using the extraction member, relative to the skin surface.

In a further embodiment of this method, after moving each of the first arm and the second arm to the skin gripping position at the skin surface, an incision can be created at the skin surface. For example, the incision can be created at the skin surface opposite the extraction member. The extraction member can be moved into contact with the skin surface adjacent the end portion of the implant after moving each of the first arm and the second arm to the skin gripping position. In this method embodiment, the implant can be moved, using the extraction member, relative to the skin surface and toward the incision.

In a further embodiment of this method, when moving the first arm from the retracted position to the skin gripping position, the skin surface can be contacted at the first side of the implant with a first skin interfacing surface of the first arm, and the skin surface can be raised at the first side of the implant. And, when moving the second arm from the retracted position to the skin gripping position, the skin surface can be contacted at the second side of the implant with a second skin interfacing surface of the second arm, and the skin surface can be raised at the second side of the implant. Raising the skin surface at the first side of the implant and raising the skin surface at the second side of the implant can include raising the implant.

The details of one or more examples are set forth in the accompanying drawings and the description below. Other features, objects, and advantages will be apparent from the description and drawings.

BRIEF DESCRIPTION OF THE DRAWINGS

The following drawings are illustrative of particular embodiments of the present invention and, therefore, do not limit the scope of the invention. The drawings are intended for use in conjunction with the explanations in the following description. Embodiments of the invention will hereinafter be described in conjunction with the appended drawings, wherein like numerals denote like elements. The features illustrated in the drawings are not necessarily to scale, though embodiments within the scope of the present invention can include one or more of the illustrated features (e.g., each of the illustrated features) at the scale shown.

DETAILED DESCRIPTION

The following detailed description is exemplary in nature and is not intended to limit the scope, applicability, or configuration of the invention in any way. Rather, the following description provides some practical illustrations for implementing embodiments of the present invention. Examples of constructions, materials, and/or dimensions are provided for selected elements. Those skilled in the art will recognize that many of the noted examples have a variety of suitable alternatives.

Figure 1:
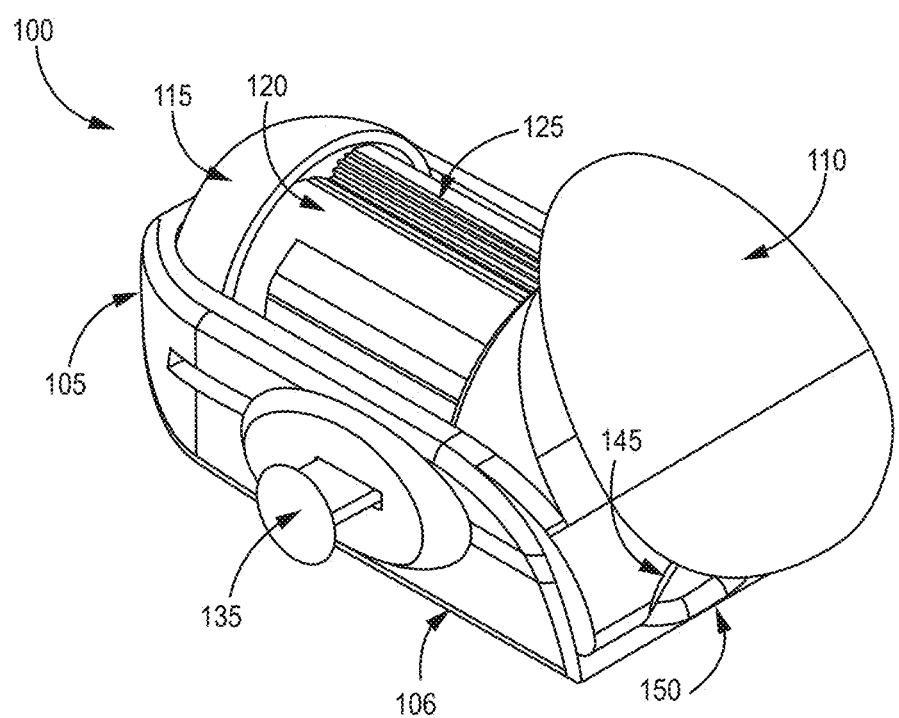
FIG. 1 is a perspective view of an embodiment of an implant removal device.
Figure 2:
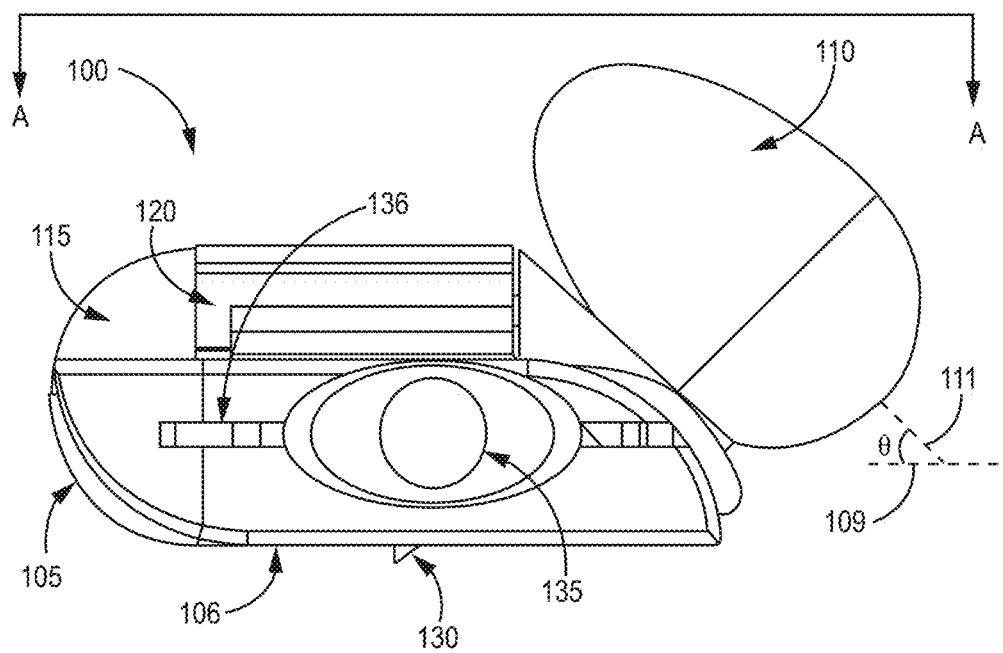
FIG. 2 is a side elevational view of the implant removal device of FIG. 1.
Figure 3:
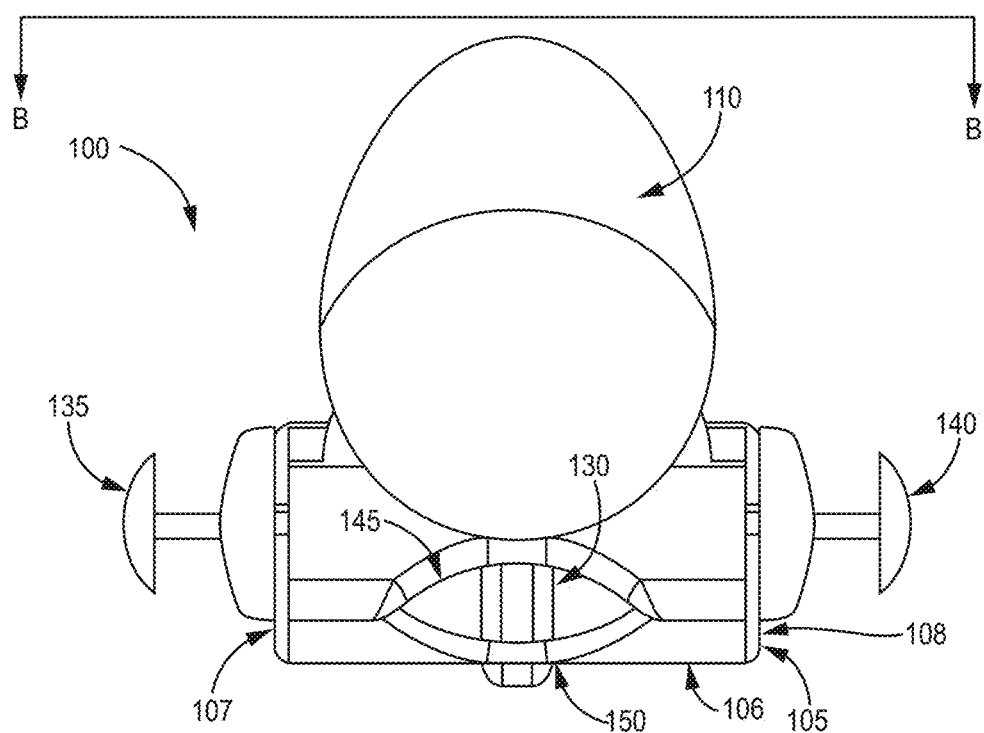
FIG. 3 is a front elevational view of the implant removal device of FIG. 1.

FIGS. 1-3 show an exemplary embodiment of an implant removal device 100. FIG. 1 illustrates a perspective view of the implant removal device 100, FIG. 2 illustrates a side elevational view of the implant removal device 100, and FIG. 3 illustrates a front elevational view of the implant removal device 100.

The implant removal device 100 can be configured to be placed at a skin surface and facilitate removal of an implant that is located beneath the skin surface (a "subdermal implant"). For example, the implant removal device 100 can be configured to facilitate removal of an elongated rod implanted beneath the skin surface and having a longitudinal axis of the elongated rod extending generally parallel to the skin surface. Such an elongated rod implant beneath the surface of the skin could be, for instance, a contraceptive subdermal implant. In operation, the implant removal device 100 can be configured to impart one or more forces at the skin surface around the subdermal implant and urge to subdermal implant out from the patient through an incision at the skin surface. For instance, in operation the implant removal device 100 can be configured to impart one or more forces at the skin surface in a direction generally perpendicular to the longitudinal axis of the elongated rod (e.g., via one or more arms of the device 100) and impart one or more forces at the skin surface in a direction generally parallel to the longitudinal axis of the elongated rod (e.g., via an extraction member of the device 100).

The illustrated implant removal device 100 includes a body 105. The body 105 includes a skin surface interfacing side 106 that can be configured to be positioned at a skin surface underneath which is an implant. For example, the body 105 can have a first lateral side 107 and a second lateral side 108, and the body 105 can be configured to be positioned such that the skin surface interfacing side 106 contacts the skin surface with the implant (located beneath the skin surface) between the first lateral side 107 and the second lateral side 108. In particular, the body 105 can be configured to be positioned such that the skin surface interfacing side 106 contacts the skin surface adjacent to an incision thereat such that the incision at the skin surface is located between the first lateral side 107 and the second lateral side 108.

The body 105 includes a handle 110 and a hand support 115. In the illustrated embodiment, the handle 110 and hand support 115 are located at opposite ends of the body 105, with the handle 110 configured to receive one hand of a user and the hand support 115 configured to receive the other hand of the user.

The handle 110 can include one or more features to facilitate operation of the device 100. First, the handle 110 can have a geometry suitable for ergonomic operation of the device 100. The handle 110 can define one or more curved surfaces. For instance, as shown in the illustrated example, the handle 110 can have a spliced ellipsoid and spherical geometry (e.g., generally egg shaped). This geometry of the handle 110 can be ergonomically suited for placement of a user's hand as it may relieve the exertion needed by certain muscles in the user's hand. For example, this geometry of the handle 110 can relieve exertion of certain muscles in the fingers and palm since the illustrated geometry of the handle 110 may not need to be tightly gripped by the user's hand to facilitate a secure control at the device 100.

Second, the handle 110 can be oriented relative to other portions of the body 105 so as to optimize the application of one or more forces applied at the device via a user's hand at the handle 110. As shown in the illustrated example, the handle 110 can be oriented at an angle $\ominus$ relative to a longitudinal axis 109 of the device 100 (e.g., an axis along which an extraction member moves). In particular, the angle $\ominus$ can be defined between a longitudinal axis 111 of the handle 110 and the longitudinal axis 109 of the device 100 and can be greater than 0 and less than or equal to 90 degrees, such as between 15 and 75 degrees, between 25 and 65 degrees, between 35 and 55 degrees, or between 40 and 50 degree (e.g., 45 degrees as shown in the illustrated example). This orientation of the handle 110 can relieve muscles in the user's forearm that are responsible for pronation and supination. This orientation of the handle 110 can also provide enhanced control over the device 100 during operation. Namely, this orientation of the handle 110 can supply force applied by a user's hand at the handle 110 into a first force component in a downward direction toward the skin surface interfacing side 106 to secure the device at the skin surface and also deform the skin surface in a manner conducive for implant removal. And, this orientation of the handle 110 can supply force applied by a user's hand at the handle 110 into a second force component in a direction toward the hand support 115 to counteract forces being applied at the body 105 to move an extraction member (as described further below), and, therefore, this second force component can act to stabilize the device 100 in place relative to the skin surface during operation.

The implant removal device 100 can include a first arm 120 and a second arm 125 each supported at the body 105. Each of the first arm 120 and the second arm 125 is movable relative to the body 105 between a retracted position and a skin gripping position. When moved relative to the body 105 to the skin gripping position, the first and second arms 120, 125 are configured to contact and raise respective skin surfaces on opposite sides of the implant. The respective ends of the arms 120, 125 configured to contact the skin surface can be closer to one another when the arms 120, 125 are at the skin gripping position than when the arms 120, 125 are at the retracted position. In the illustrated example, the first and second arms 120, 125 each pivot about the body 105, though in other embodiments the arms 120, 125 could move relative to the body 105 in other manners. The arms 120, 125 will be described in more detail further below.

The implant removal device 100 further includes an extraction member 130 supported at the body 105. The extraction member 130 is movable relative to the body 105 between an implant engagement position and an implant removal position. When moved relative to the body 105 from the implant engagement position toward the implant removal position, the extraction member 130 is configured to urge the implant toward an incision at the skin surface. The implant removal position of the extraction member 130 is closer to the handle 110 than the implant engagement position. In the illustrated example, the extraction member 130 slides relative to the body 105, though in other embodiments the extraction member 130 could move relative to the body 105 in one or more other manners. The extraction member 130 will be described in more detail further below.

The implant removal device 100 additionally includes one or more buttons to actuate one or more of the arms 120, 125 and/or the extraction member 130. In the illustrated example, the device 100 includes a first button 135 and a second button 140. Each of the first button 135 and the second button 140 is located at the body 105. The buttons 135, 140 can, in some embodiments, be covered by a button interface layer. For example, the button interface layer over the buttons 135, 140 can be made of a material including silicone to provide both comfort and stability when contacted by a user (e.g., a user's fingers).

In the illustrated embodiment, the first and second buttons 135, 140 can be actuated to move the first and second arms 120, 125 between the retracted and skin gripping positions. For example, when a first actuation input is applied at the first button 135, the first button 135 is configured to move the first arm 120 from the retracted position to the skin gripping position. Also in this example, when the first actuation input is applied at the second button 140, the second button 140 is configured to move the second arm 125 from the retracted position to the skin gripping position. For instance, the first actuation input can be a force applied by a user's finger to push the respective button 135, 140 inward toward the respective lateral side 107, 108. In this way, a user can utilize one hand (e.g., placed at the hand support 115) to actuate each of the buttons 135, 140 to bring the arms 120, 125 into the skin gripping position. In one embodiment, the arms 120, 125 can be biased (e.g., spring biased) to the retracted position and applying the first actuation input at the respective button 135, 140 can overcome the bias on the respective arm 120, 125 and bring it to the skin gripping position. For example, a coil (e.g., torsional) spring or a constant force spring could be used to provide the bias force on a respective arm 120, 125. In one instance, a constant force spring can be mounted on a rod at the device 100 acting as a spool mount and apply the bias force on a respective arm 120, 125. Likewise, in this embodiment, once the first actuation input is removed from the respective button 135, 140, the respective arm 120, 125 can be returned to the retracted position by the bias force on the respective arm 120, 125. Other examples of the first actuation input can include other forces applied by a user's finger at the respective button 135, 140, such as to pull the respective button 135, 140 outward away from the respective lateral side 107, 108, or push the respective button 135, 140 upward or downward. In some embodiments, the device 100 can be configured such that applying the first actuation input at one of the buttons 135, 140 can cause both of the arms 120, 125 to move the first and second arms 120, 125 between the retracted and skin gripping positions.

In addition, in the illustrated embodiment, the first and/or second button 135, 140 can be actuated to move the extraction member 130 between the implant engagement position and the implant removal position. In the illustrated embodiment, the first and second buttons 135, 140 can be actuated to move the extraction member 130 between the implant engagement position and the implant removal position. For example, when a second actuation input is applied at the first and second buttons 135, 140, the first and the second buttons are configured to move the extraction member 130 from the implant engagement position toward the implant removal position. For instance, the second actuation input can be a force applied by a user's respective fingers at the buttons 135, 140 to slide the buttons 135, 140 relative to the respective lateral sides 107, 108. The buttons 135, 140 can be configured such that applying the second actuation input to slide the buttons 135, 140 toward the handle 110 can cause the extraction member 130 to move from the implant engagement position toward the implant removal position. To facilitate sliding actuation of the buttons 135, 140, the body 105 can define a button slide slot 136 at each lateral side 107, 108. Other examples of the second actuation input can include other forces applied by a user's finger at the respective button 135, 140. In some embodiments, the device 100 can be configured such that applying the second actuation input at either of the buttons 135, 140 can cause the extraction member 130 to move between the implant engagement position and the implant removal position.

Thus, in operation, the device 100 can be configured to facilitate removal of a subdermal implant upon actuation of one, or both, of the buttons 135, 140. For example, a user can first apply the first actuation input at the button 135 and/or 140 to bring the arms 120, 125 to the skin gripping position. Bringing the arms 135, 140 to the skin gripping position can cause the skin surface on each side of the implant and between the lateral sides 107, 108 to be raised, and, thus also raising the implant. Then, while the first actuation input is continuing to be applied at the button 135 and/or 140 such that the arms 120, 125 are at the skin gripping position, a user can apply the second actuation input at the button 135 and/or 140 to bring the extraction member 130 toward the implant removal position. Bringing the extraction member 130 toward the implant removal position can cause the raised implant to be moved, underneath the skin surface, toward the incision at the skin surface (e.g., moved toward to handle 110). Continued movement of the extraction member 130 toward the implant removal position can continue to urge the implant closer to the incision at the skin surface. As such, in this example, the user can use one finger at the button 135 and one finger at the button 140 to bring the arms 120, 125 to the skin gripping position (e.g., by pushing the buttons 135, 140) and then bring the extraction member toward the implant removal position while the arms 120, 125 are kept at the skin gripping position (e.g., by sliding the buttons 135, 140 while pushing the buttons 135, 140).

To further assist in removing the subdermal implant, the implant removal device 100 can also include a guide slot 145 and a force imparting interface 150. The guide slot 145 and force imparting interface 150 are each defined at the body 105. Each of the guide slot 145 and the force imparting interface 150 can be aligned and, as such, located on a common radial axis of the implant removal device 100 (e.g., the radial axis of the device being perpendicular to a longitudinal axis of the device 100, such as the radial axis being perpendicular to an axis along which the extraction member 130 moves between the implant engagement and implant removal positions). The force imparting interface 150 can be configured to contact the skin surface, such as the skin surface interfacing with an end of the incision (e.g., such that the incision is bounded by the lateral sides 107, 108 and the forward wall of the body 105 at which the guide slot 145 is defined). As shown in the illustrated embodiment, the guide slot 145 and force imparting interface 150 can be aligned at the body 105 with the handle 110 (e.g., a common radial axis of the implant removal device 100 extends through each of the guide slot 145, the force imparting interface 150, and the handle 110). As such, when a force is applied at the handle 110 via a user's hand (e.g., the user's hand not at the buttons 135, 140), the force imparting interface 150 can be configured to push this skin surface thereat downward, bringing at least a portion of the incision into alignment with the guide slot 145. In this way, the handle 110 and force imparting interface 150 can help to remove the implant through the incision and out through the guide slot 145 by reducing the likelihood that, as the implant is moved underneath the skin surface by the extraction member 130, the implant misses the incision and passes under the guide slot 145.

Further details pertaining to the arms 120, 125, the extraction member 130, and related components are described as follows.

Figure 4:
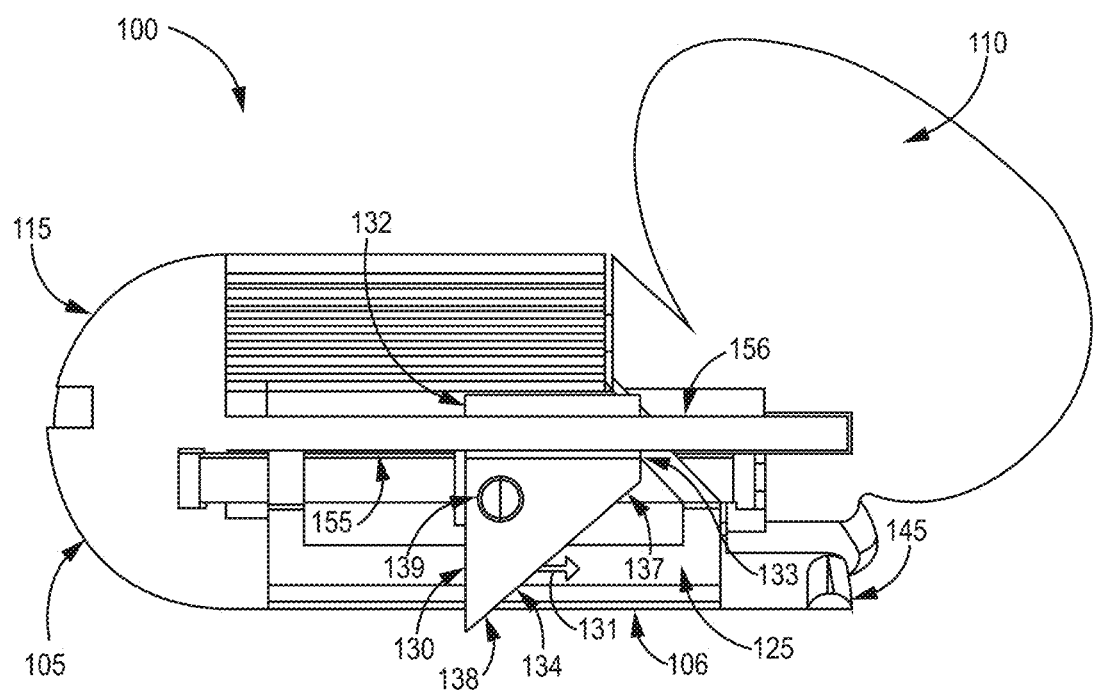
FIG. 4 is a longitudinal cross-sectional view of the implant removal device of FIG. 1, taken along longitudinal line A-A in FIG. 2.

FIG. 4 illustrates a longitudinal cross-sectional view of the implant removal device 100, taken along longitudinal line A-A in FIG. 2. In the embodiment shown, the device 100 includes an extraction support 155. The extraction member 130 can be movably coupled to the extraction support 155 such that the extraction member 130 moves along the extraction support between the implant engagement position and the implant removal position. The implant engagement position can be closer to the hand support 115 than the implant removal position, and the implant removal position can be closer to the handle 110 than the implant engagement position. Accordingly, the extraction member 130 can move along the extraction support 155 from the implant engagement position toward the implant removal position in a direction 131, and vice versa.

To stabilize the extraction member 130 at the extraction support 155, the extraction support 155 and the extraction member 130 can each have complementary geometric features that act together to allow the extraction member 130 to move along the extraction support 155 in a direction parallel to a longitudinal axis of the extraction support 155 (e.g., the direction 131) but restrict rotational movement of the extraction member 130 about the longitudinal axis of the extraction support 155. As such, the complementary geometric features of the extraction member 130 and the extraction support 155 can stabilize the extraction member 130 and can thereby facilitate movement of the extraction member 130 along the extraction support 155 from the implant engagement position toward the implant removal position in the direction 131. For instance, the extraction support 155 and the extraction member 130 can each have complementary cross-sectional shapes that act together to allow the extraction member 130 to move along the extraction support 155 in a direction parallel to a longitudinal axis of the extraction support 155 (e.g., the direction 131) but restrict rotational movement of the extraction member 130 about the longitudinal axis of the extraction support 155. In one such embodiment, the extraction support 155 and the extraction member 130 can each have ellipsoidal complementary cross-sectional shapes. In this particular embodiment, the oblong component of the ellipsoidal complementary cross-sectional shapes can restrict rotation of the extraction member 130 about the longitudinal axis of the extraction support 155 and, at the same time, can provide an increased cross sectional area at the extraction member 130 that can make the extraction member 130 more rigid to resist the forces during implant removal.

In one such example, to stabilize the extraction member 130 at the extraction support 155, the extraction support 155 and the extraction member 130 can each have complementary keyed interfacing surfaces. For example, the extraction member 130 can include a keyed surface 132 and the extraction support 155 can include a keyed surface 156, and the keyed surfaces 132, 156 can interface with one another. For instance, one of the keyed surfaces 132, 156 can form a protruded flange extending outward from one of the respective extraction member 130 and the extraction support 155 while the other of the keyed surfaces 132, 156 can form a recessed slot extending inward into the other of the respective extraction member 130 and the extraction support 155. In the illustrated embodiment, the extraction member 130 defines a slot 133 therethrough, and the slot 133 includes the keyed surface 132. Also in the illustrated embodiment, the keyed surface 156 of the extraction support 155 is included at a surface of the extraction support 155 that interfaces with the slot 133 as the extraction member 130 moves along the extraction support 155. The keyed surfaces 132, 156 can be complementary and configured to allow the extraction member 130 to move along the extraction support 155 in a direction parallel to a longitudinal axis of the extraction support 155 (e.g., the direction 131) but restrict rotational movement of the extraction member 130 about the longitudinal axis of the extraction support 155. As such, the complementary keyed surfaces 132, 156 can stabilize the extraction member 130 and can thereby facilitate movement of the extraction member 130 along the extraction support 155 from the implant engagement position toward the implant removal position in the direction 131.

The extraction member 130 can include a skin contact surface 134 that is configured to contact the skin surface at which the device 100 is placed and move the implant underneath the skin surface. As shown here, the skin contact surface 134 can extend at an angle from an upper portion 137 of the extraction member 130 to a lower portion 138 of the extraction member 130. The angle at which the skin contact surface 134 extends can be angled relative to the direction 131 (e.g., angled relative to the longitudinal axis of the extraction support 155). For example, the skin contact surface 134 can extend at an angle, relative to the direction 131 in which the extraction member 130 travels from the implant engagement position toward the implant removal position, greater than 0 and less than 90 degrees, such as between 15 and 75 degrees, between 25 and 65 degrees, between 35 and 55 degrees, or between 40 and 50 degree (e.g., 45 degrees as shown in the illustrated example). The angled skin contact surface can be useful in reducing patient discomfort, such as by reducing the likelihood of damage to the skin surface, by facilitating the passage of skin underneath the extraction member 130 as the extraction member 130 moves along the skin surface in the direction 131 from the from the implant engagement position toward the implant removal position to urge the implant toward the guide slot 145.

The extraction member 130 can also include an arm support 139. The arm support 139 can be configured to couple to a slidable mount 141, 142 of one, or both, of the arms 120, 125 (shown, e.g., in FIG. 5). In the illustrated embodiment, the arm support 139 is in the form of an aperture extending through the extraction member 130. The arm support 139 can receive the slidable mount(s) 141, 142 from the arms 120, 125 and allow the slidable mount(s) to move within the arm support 139 relative to the extraction member 130. For example, the arm support 139 can receive one slidable mount 141 of the first arm 120 therein and another slidable mount 142 of the second arm 125 therein, and each of these slidable mounts 141, 142 can translate within the arm support 139, and relative to the extraction member 130, as the respective arm 120, 125 moves between the retracted and skin gripping positions as a result of the first actuation input applied at the respective buttons 135, 140.

Figure 5:
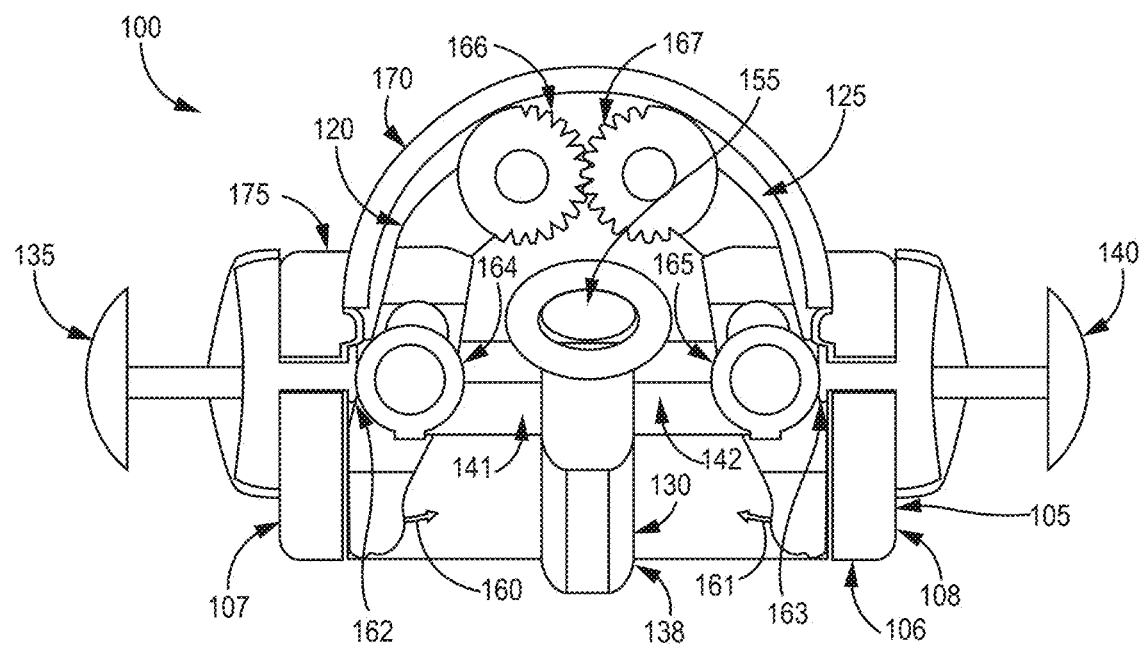
FIG. 5 is a radial cross-sectional view of the implant removal device of FIG. 1, taken along radial line B-B in FIG. 3.

FIG. 5 is a radial cross-sectional view of the implant removal device 100, taken along radial line B-B in FIG. 3. As noted, the device 100 can include the first arm 120 and the second arm 125. Applying the first actuation input at the first button 135 can move the first arm 120 in a direction 160 from the retracted position, shown in FIG. 5, to the skin gripping position. And, applying the first actuation input at the second button 140 can move the second arm 125 in a direction 161 from the retracted position, shown in FIG. 5, to the skin gripping position.

In the illustrated embodiment, the buttons 135, 140 are configured to cause the arms 120, 125 to move from the retracted position to the skin gripping position via a first rotational joint 164 that couples the first button 135 to the first arm 120 and a second rotational joint 165 that couples the second button 140 to the second arm 125. In particular, the first button 135 includes a first shaft 162 that interfaces with (e.g., contacts) the first rotational joint 164, and the second button 140 includes a second shaft 163 that interfaces with (e.g., contacts) the second rotational joint 165. Applying the first actuation input at the first button 135 can cause the first shaft 162 to translate the slidable mount 141 within the arm support 139 and rotatably move the first rotational joint 164 which in turn causes the first arm 120 to pivot in the direction 160 to the skin gripping position. Likewise, applying the first actuation input at the second button 140 can cause the second shaft 163 to translate the slidable mount 142 within the arm support 139 and rotatably move the second rotational joint 165 which in turn causes the second arm 125 to pivot in the direction 161 to the skin gripping position. As shown in the illustrated example, the first and second arms 120, 125 can include complementary teeth 166, 167 that mesh together as the first and second arms 120, 125 pivot to the skin gripping positions.

As also shown in FIG. 5, the body 105 can include an upper housing portion 170 and a lower housing portion 175. The lower housing portion 175 includes the skin surface interfacing side 106 as well as the first lateral side 107 and the second alter side 108. As such, the lower housing portion 170 can define the volume within which the skin surface is raised, via the arms 120, 125, and the implant is moved, via the extraction member 130. The upper housing portion 170 can define the hand support 115 and can extend out above the tops of the arms 120, 125 and enclose the arms 120, 125. In one embodiment, both the lower housing portion 174 and the upper housing portion 170 can be made of a transparent material (e.g., a transparent polymer material, such as polycarbonate material). In this embodiment, a user of the device may be able see components of the device 100, as well as the skin surface overlaying the implant, during the implant removal procedure. In another embodiment, the lower housing portion 174 can be made of a non-transparent outer material while the upper housing portion 170 can be made of a transparent material. In some examples, the hand support region of the upper housing portion 170 can be made of a non-transparent material while the remainder of the upper housing portion 170 can be made of a transparent material. The described configurations of the upper housing portion 170 and the lower housing portion 175 can be useful in facilitating user (e.g., clinician) visibility of the implant removal procedure while at the same time obstructing (e.g., shielding) the patient's view of the implant removal procedure. Namely, the transparent areas of the upper housing portion 170 can facilitate user visibility of the procedure while the non-transparent areas of the lower housing portion 175, handle 110, and hand support 115 can obstruct the patient's view of the implant removal procedure. Since the implant removal procedure is generally performed with only local anesthesia, this configuration of the device 100 can be conducive to increasing the patient's comfort during the procedure.

Figure 6:
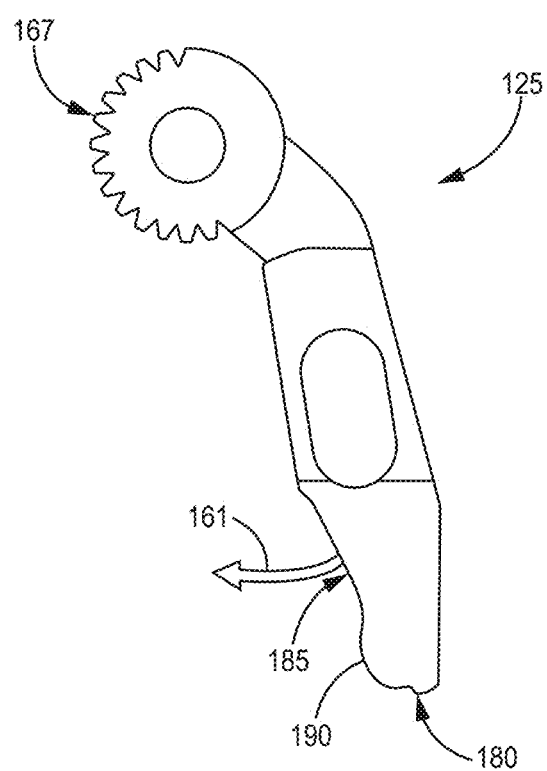
FIG. 6 is a front elevational view of an arm of the implant removal device of FIG. 1.

FIG. 6 illustrates a front elevational view of the second arm 125 of the implant removal device 100. It is to be understood that the features disclosed with respect to the second arm 125 can also apply to the first arm 120 in the same, or similar, manner. The arms 120, 125 can move from the retracted position to the skin gripping position (e.g., the direction 161 for the second arm 125) at an angle of rotation that results in a scooping movement along the skin surface. The arms 120, 125 can define a geometric configuration that is conducive to applying suitable force at the skin surface to achieve the desired skin raising and implant positioning while also distributing force in a manner that reduces discomfort to the patient as the arms 120, 125 move along the skin surface.

As shown in FIG. 6, the arm 125 includes a protruded edge 180. This protruded edge 180 can be at a location on the arm 125 that is configured to contact the skin surface. The protruded edge 180 can define a surface area configured to increase local pressure at the skin surface contacting the protruded edge 180. In particular, the protruded edge 180 extends out a relatively small extent from a bottom end portion of the arm 125 and, therefore, can be configured to increase local pressure to locally deform the skin surface in contact thereat while also reducing the amount of the skin surface that is deformed. As one example, the protruded edge 180 can extend out from a bottom end portion of the arm 125 a distance that approximates, for instance that is equal to or less than, a cross-sectional area of the implant that the device 100 is configured to remove. As a result, this protruded edge 180 can facilitate raising the skin surface and forming a suitable shape of this raised skin surface for removing the implant.

The arm 125 can also include a concave region 185 and a convex region 190. The concave region 185 can be geometrically concave and the convex region can be geometrically convex relative to the surface of the arm 125 facing the extraction member 130. In the illustrated embodiment, the convex region 190 is between the concave region 185 and the protruded edge 180 along the inner surface of the arm 125.

As the arm 125 moves in the direction 161 toward the skin gripping position, the arm 125 will act to scoop the skin surface and continually increase the depth relative to the skin surface through the angle of movement in the direction 161 toward the skin gripping position. This scooping function can raise the implant and place the protruded edge 180 at a lower depth at the tissue surface than the raised implant. The concave region 185 can be configured to provide a support force on the raised skin surface in a generally upward direction (e.g., toward the teeth 167), which can help to maintain the implant in a raised position and, thereby, reduce the likelihood that the scooping movement of the arm 125 pushes the implant downward. The convex region 190 can be configured to position the raised skin out of the path of movement of the extraction member 130 and, thereby, reduce the likelihood that the raised skin surface will be damaged (e.g., pinched) by the moving extraction member 130. Moreover, the curvature along the convex region 190 as it transitions to the protruded edge 180 can be configured to incrementally increase the local pressure applied at the skin surface as the arm 125 is moved in the direction 161. Once the arm 125 has been moved to the skin gripping position, and thus the skin surface and underlying implant have been raised by the arm 125, the extraction member 130 can be moved toward the implant removal position and act to urge the implant along with it underneath the skin surface and toward the incision at the skin surface (e.g., adjacent the guide slot 145).

Figure 7:
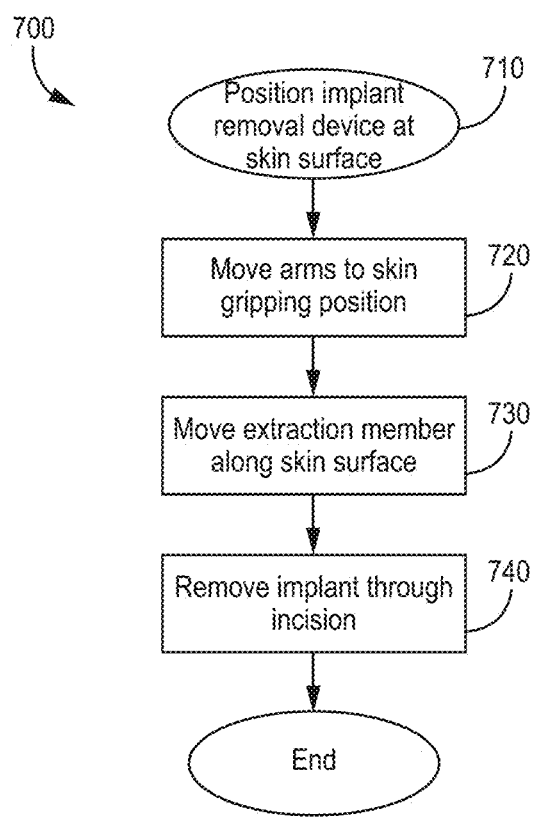
FIG. 7 is a flow diagram of an embodiment of a method of removing an implant (e.g., a subdermal implant).

FIG. 7 is a flow diagram of an embodiment of a method of removing a subdermal implant. The method 700 can be performed using an implant removal device having one or more of the features (e.g., each of the features) disclosed herein. For example, the method 700 can be performed using the implant removal device 100.

At step 710, the method 700 includes positioning an implant removal device at a skin surface. As noted, in one example, the implant removal device positioned at step 710 can be the implant removal device 100 described herein. The skin surface at which the implant removal device is positioned can overlay a subdermal implant. The implant removal device can be positioned at this skin surface such that lateral sides of the implant removal device are spaced from the location of the implant on opposite longitudinal sides of the implant. And, the implant removal device can be positioned at this skin surface such that such that a guide slot defined at a body of the implant removal device is aligned with a region of the skin surface interfacing with an end of the incision (e.g., such that the incision is bounded by the lateral sides and the forward wall of the implant removal device's body at which the guide slot is defined).

At step 720, the method 700 includes moving one or more arms, of the positioned implant removal device, to a skin gripping position. For example, this could include moving both a first arm and a second arm, relative to a body of the implant removal device, from a retracted position to a skin gripping position. For example, a user can apply a first actuation input at a first button (e.g., via a first finger of one hand) to bring the first arm to the skin gripping position and apply the first actuation input at a second button (e.g., via a second finger of the one hand) to bring the second arm to the skin gripping position. When moved to the skin gripping position, the first and second arms are configured to contact and raise respective skin surfaces on opposite sides of the implant, thus also raising the implant.

At step 730, the method 700 includes moving an extraction member of the positioned implant removal device along the skin surface. In this method embodiment, the extraction member is moved, relative to the body of the implant removal device, from an implant engagement position toward an implant removal position while the one or more arms are at the skin gripping position. For example, a user can apply a second actuation input at the first and/or second button to slide the extraction member relative to the body of the implant removal device. The second actuation input can be different than the first actuation input, for instance applied in a different direction than the first actuation input (e.g., the second actuation input can be applied in a direction generally perpendicular to the first actuation input). The second actuation input can be applied while the first actuation input continues to be applied such that the extraction member slides toward the implant removal position while the first and second arms are kept at the skin gripping position. As the extraction member is moved from the implant engagement position toward the implant removal position, the extraction member can move along the skin surface and, in doing so, urge the implant, underneath the skin surface, toward the incision. For example, as the extraction member moves from the implant engagement position toward the implant removal position, the extraction member can move between the first and second arms that are at the skin gripping position.

At step 740, the method 700 includes removing the implant through the incision at the skin surface. For example, the implant can be urged out from underneath the skin surface and through the incision by the extraction member, as it is moved to the implant removal position. In one embodiment, the implant removal device can include a handle, a guide slot, and a force imparting interface each defined, and generally aligned, at the implant removal device's body. The force imparting interface can contact the skin surface, such as the skin surface interfacing with an end of the incision. A force can be applied at the handle via a user's hand (e.g., the user's hand not at the first and second buttons) to cause the force imparting interface to push this skin surface in contact thereat downward, bringing at least a portion of the incision into alignment with the guide slot. In this way, the handle and force imparting interface can help to appropriately align the incision and implant while the extraction member is being moved, and thus urging the implant toward the incision, and, thereby, help to remove the implant through the incision and out through the guide slot. When the implant has been removed from underneath the skin surface (e.g., through the guide slot), the implant removal device can be removed from the skin surface and the incision can be closed.

Figure 8:
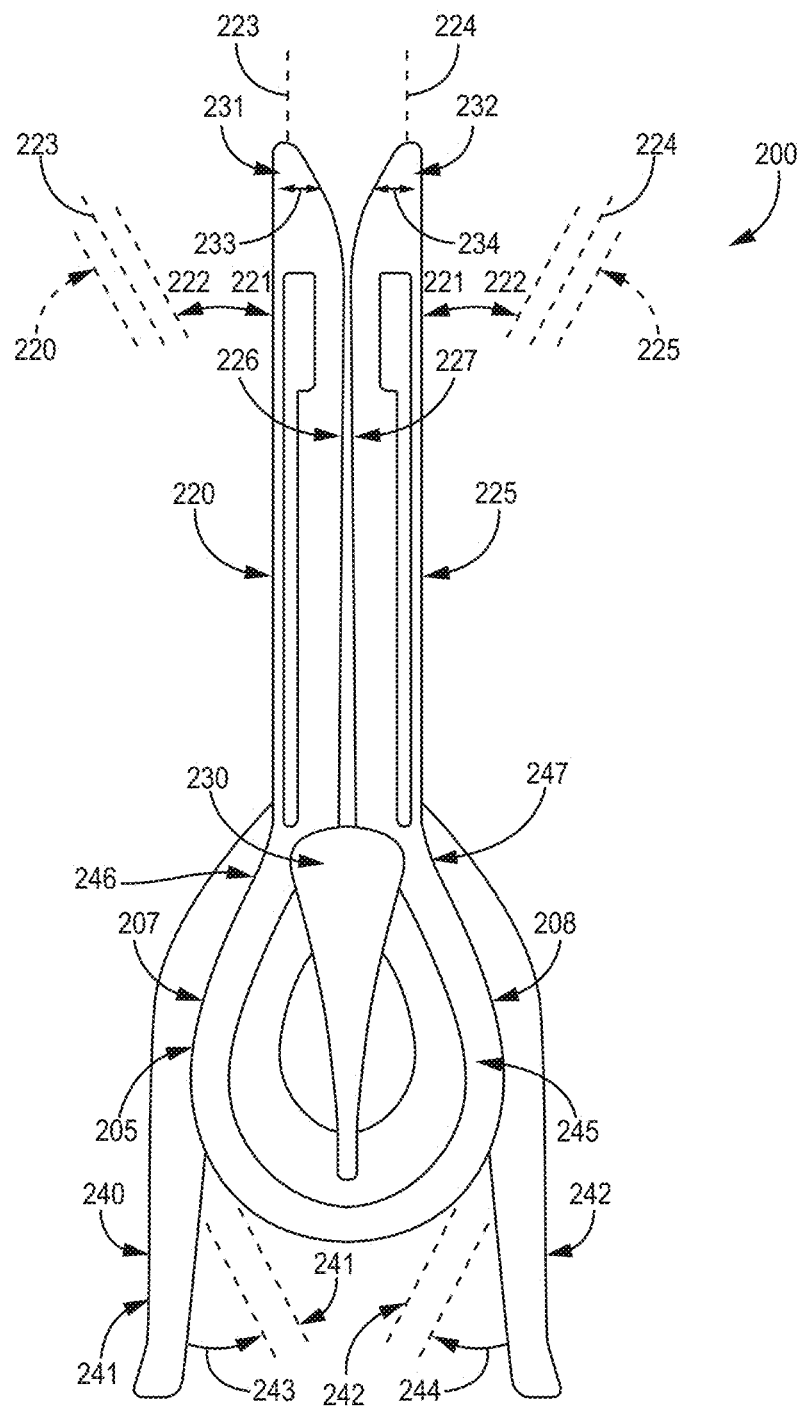
FIG. 8 is a plan view of another embodiment of an implant removal device.
Figure 9:
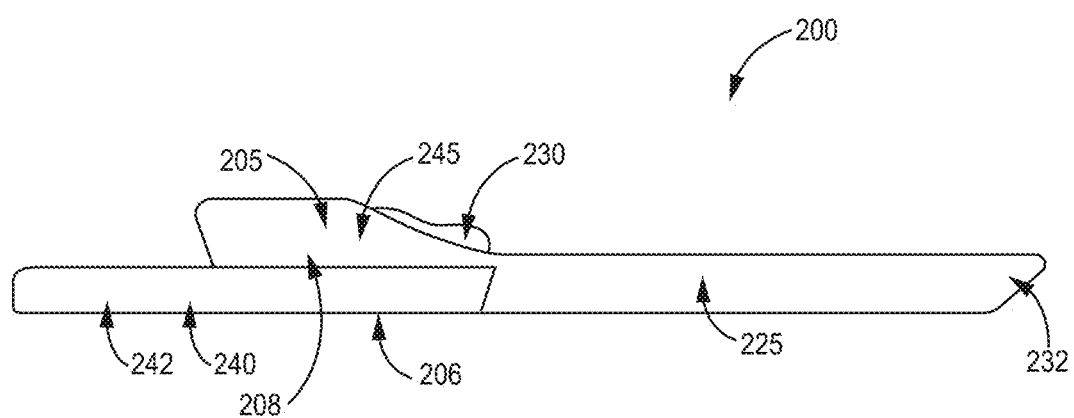
FIG. 9 is a side elevational view of the implant removal device of FIG. 8.
Figure 10:
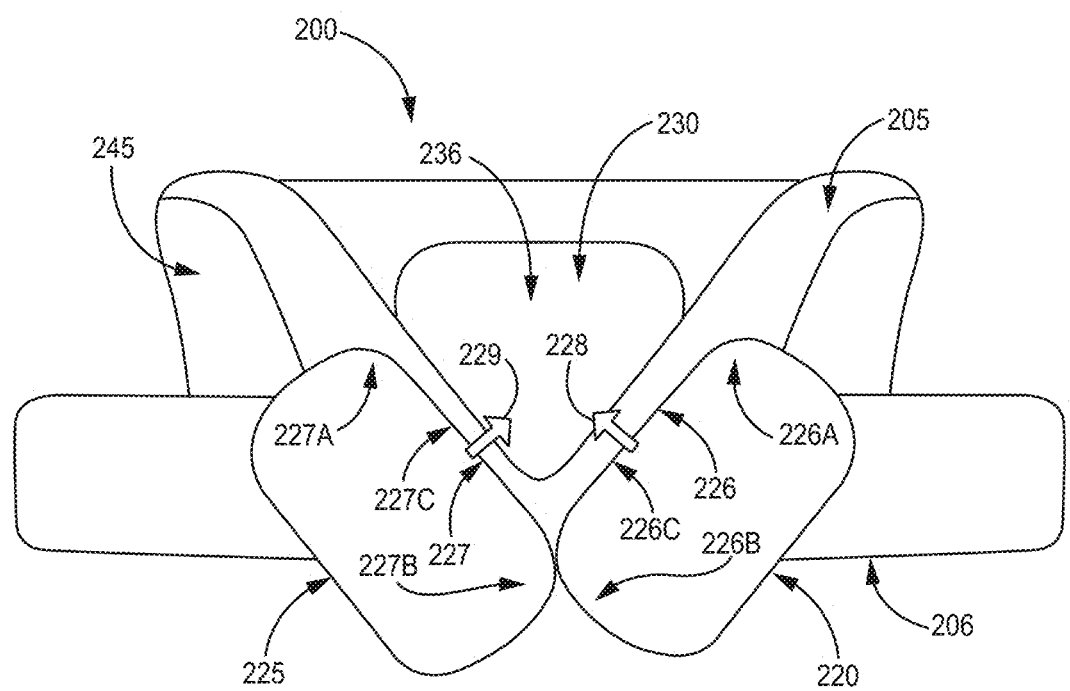
FIG. 10 is an end elevational view of the implant removal device of FIG. 8.
Figure 11:
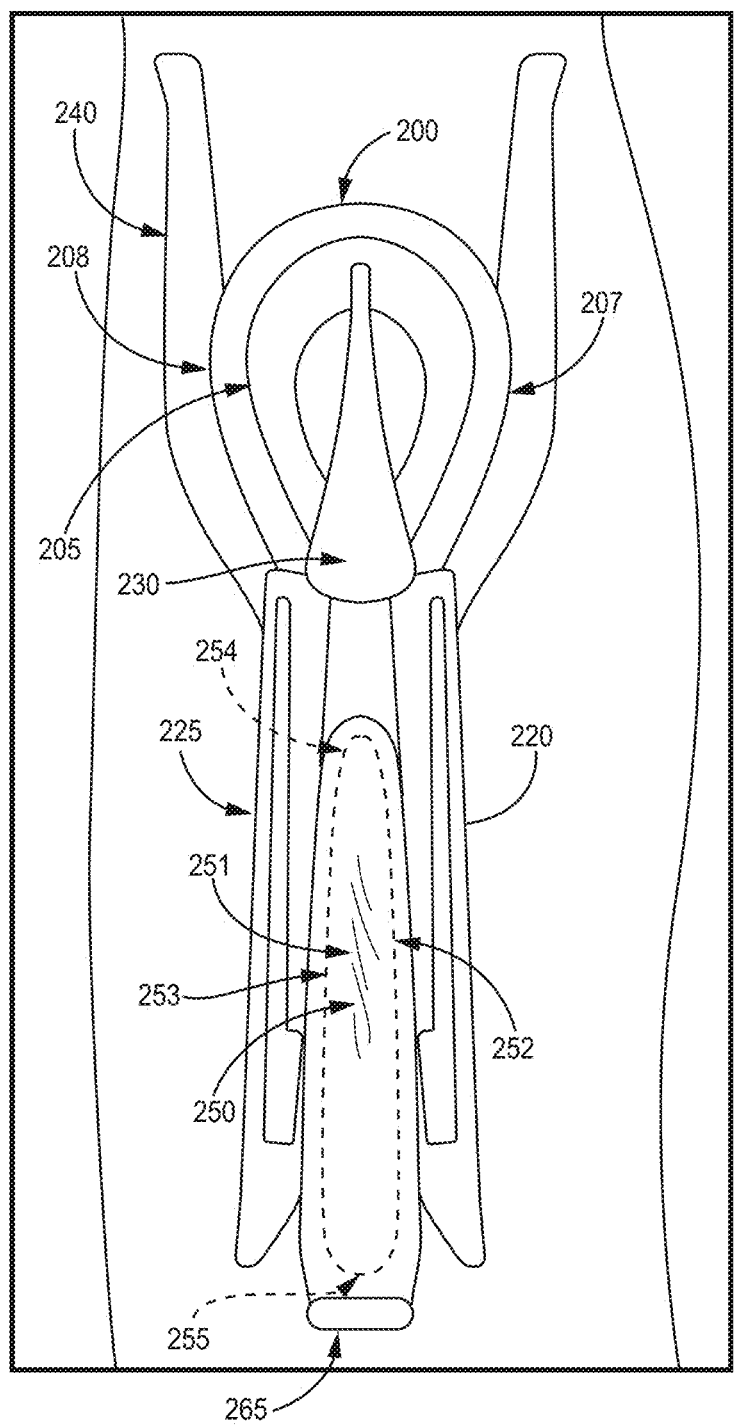
FIG. 11 is a perspective view of the implant removal device of FIG. 8 positioned at a skin surface that includes a subdermal implant.
Figure 12:
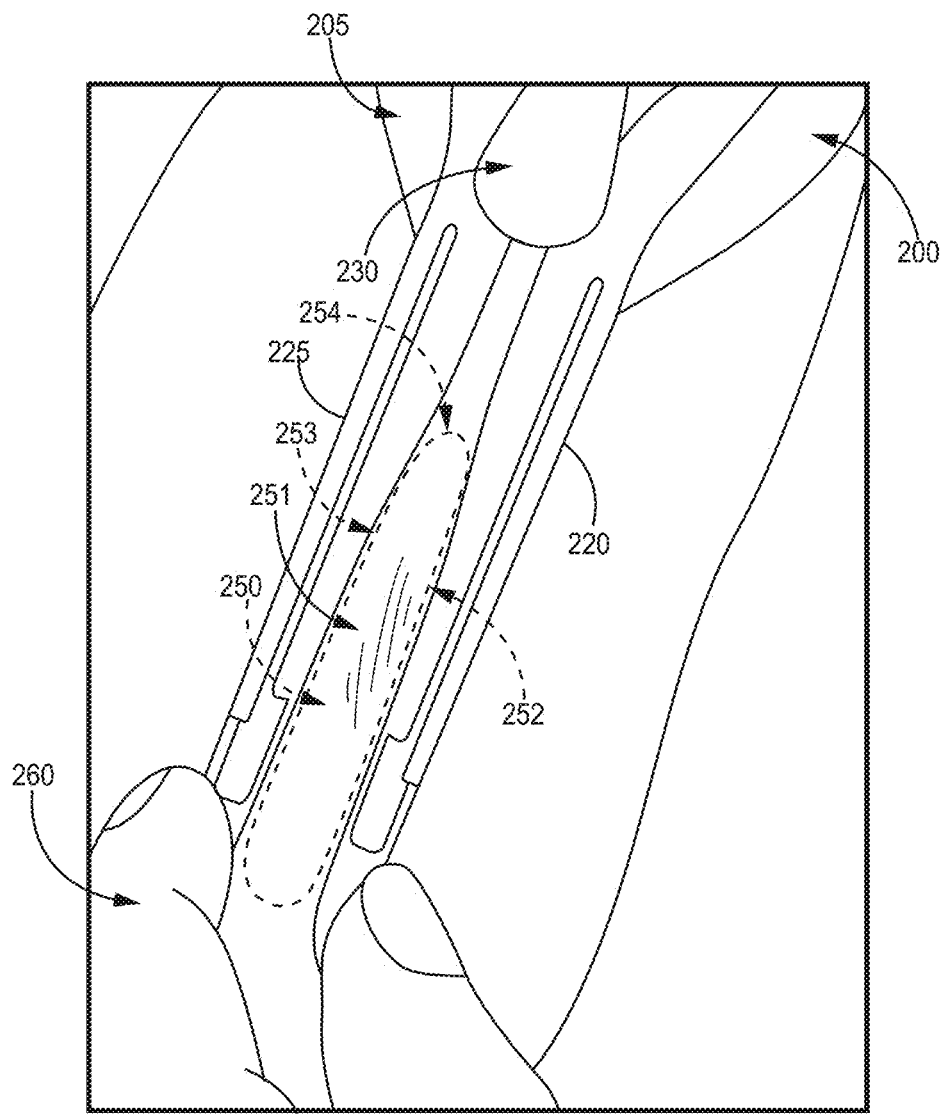
FIG. 12 is a close-up perspective view of the implant removal device of FIG. 11 with first and second arms of the device being held by a hand of a user.
Figure 13:
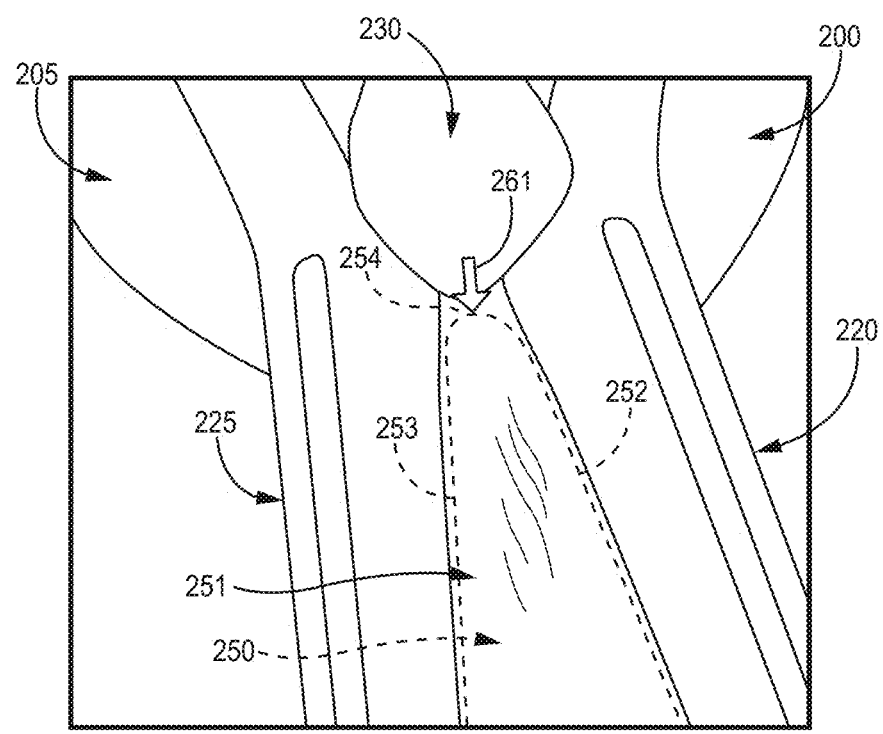
FIG. 13 is a close-up perspective view of the implant removal device of FIG. 11 but with an extraction member of the device moved into engagement with the skin surface adjacent an end portion of the implant.

FIGS. 8-13 illustrate another embodiment of an implant removal device 200. In particular, FIGS. 8-10 show the implant removal device 200 in isolation, while FIGS. 11-13 shown the implant removal device 200 positioned at a skin surface having an implant (e.g., a subdermal implant). Features, and related operation, of the implant removal device 200 will be described as follows. It is to be noted that, in some embodiments, the implant removal device 200 can include any one or more of the features described previously herein with respect to the implant removal device 100.

As noted, FIGS. 8-10 show the implant removal device 200 in isolation. Specifically, FIG. 8 is a plan view of the implant removal device 200, FIG. 9 is a side elevational view of the implant removal device 200, and FIG. 10 is an end elevational view of the implant removal device 200. The illustrated embodiment of the implant removal device 200 is a single, integral piece device. As such, the device 200 may not have removable connections between the various components. In other embodiments within the scope of the present disclosure, the device 200 can be a multi-piece device with removable connections between two or more various components.

Like the implant removal device 100, the implant removal device 200 can be configured to be placed at a skin surface and facilitate removal of an implant that is located beneath the skin surface (a "subdermal implant"). For example, the implant removal device 200 can be configured to facilitate removal of an elongated rod implanted beneath the skin surface and having a longitudinal axis of the elongated rod extending generally parallel to the skin surface. Such an elongated rod implant beneath the surface of the skin could be, for instance, a contraceptive subdermal implant. In operation, the implant removal device 200 can be configured to impart one or more forces at the skin surface adjacent to (e.g., around portions of) the subdermal implant and urge to subdermal implant out from the patient through an incision at the skin surface. For instance, in operation the implant removal device 200 can be configured to impart one or more forces at the skin surface in a direction generally perpendicular to the longitudinal axis of the elongated rod (e.g., via one or more arms of the device 200) and impart one or more forces at the skin surface in a direction generally parallel to the longitudinal axis of the elongated rod (e.g., via an extraction member of the device 200).

The illustrated implant removal device 200 includes a body 205. The body 205 includes a skin surface interfacing side 206 that can be configured to be positioned at a skin surface adjacent to, and underneath which is, an implant. For example, the body 205 can have a first lateral side 207 and a second lateral side 208, and the body 205 can be configured to be positioned such that the skin surface interfacing side 206 contacts the skin surface with the implant (located beneath the skin surface) between the first lateral side 207 and the second lateral side 208. In particular, when an incision is made at the skin surface, the body 205 can be configured to be positioned such that the skin surface interfacing side 206 contacts the skin surface adjacent to an incision thereat such that the incision at the skin surface is located between the first lateral side 207 and the second lateral side 208.

The implant removal device 200 can include a first arm 220 and a second arm 225 each supported at the body 205. The first arm 220 can define a first arm longitudinal axis 223 along which a length of the first arm 220 extends, and the second arm 225 can define a second arm longitudinal axis 224 along which a length of the second arm 225 extends. Each of the first arm 220 and the second arm 225 is movable relative to the body 205 between a retracted position 222 and a skin gripping position 221. In the illustrated example, the first and second arms 220, 225 each pivot relative to the body 205, though in other embodiments the arms 220, 225 could move relative to the body 205 in other manners. As described further below, each of the first and second arm 220, 225 can be biased to the skin gripping position 221. FIG. 8 shows the first and second arms 220, 225 in one exemplary skin gripping position 221, and FIG. 8 includes dashed lines to illustrate one exemplary retracted position 222. As this exemplary illustration shows, a space defined between the first arm 220 and the second arm 225 can be greater when the first and second arm 220, 225 are in the retracted position 222 than when the first and second arm 220, 225 are in the skin gripping position 221. When moved relative to the body 205 to the skin gripping position 221, the first and second arms 220, 225 are configured to contact and raise respective skin surfaces on opposite sides of the implant.

As best seen in FIG. 10, the first arm 220 can include a first skin interfacing surface 226 and the second arm 225 can include a second skin interfacing surface 227. The first skin interfacing surface 226 can include a first skin interfacing surface first convex region 226A at an upper portion (e.g., generally opposite the skin surface interfacing side 206) of the first arm 220 and a first skin interfacing surface second convex region 226B at a lower portion (e.g., at the skin surface interfacing side 206) of the first arm 220. The first skin interfacing surface 226 can further include a first skin interfacing surface planar region 226C that interconnects the first skin interfacing surface first convex region 226A and the first skin interfacing surface second convex region 226B. Likewise, the second skin interfacing surface 227 can include a second skin interfacing surface first convex region 227A at an upper portion (e.g., generally opposite the skin surface interfacing side 206) of the second arm 225 and a second skin interfacing surface second convex region 227B at a lower portion (e.g., at the skin surface interfacing side 206) of the second arm 225. The second skin interfacing surface 227 can further include a second skin interfacing surface planar region 227C that interconnects the second skin interfacing surface first convex region 227A and the second skin interfacing surface second convex region 227B. Each of the noted lower portions of the first and second arms 220, 225 can be opposite each of the respective noted upper portions of the first and second arms 220, 225.

As illustrated in this exemplary embodiment, the first skin interfacing surface 226 and the second skin interfacing surface 227 can face toward one another. The first skin interfacing surface 226 and the second skin interfacing surface 227 can each work together to apply one or more forces, at the skin surface adjacent the implant, to stabilize and position the implant for efficient removal. For example, when the arms 220, 225 are moved to the skin gripping position 221, such as shown in FIG. 10, the arms 220, 225 can contact and raise respective skin surfaces on opposite sides of the implant so as to thereby raise and position the implant between the first skin interfacing surface 226 and the second skin interfacing surface 227.

More specifically, each of the first skin interfacing surface first and second convex regions 226A, 226B and the second skin interfacing surface first and second convex regions 227A, 227B can allow excess skin at the skin surface to pass away from the interfacing first and second skin interfacing surfaces 226, 227 and, thereby, provide a more precise and stable positioning of the implant beneath this skin surface. In addition, the first skin interfacing surface planar region 226C, of first skin interfacing surface 226, can apply a stabilizing force 228 in a direction generally normal to the first skin interfacing surface planar region 226C. Likewise, the second skin interfacing surface planar region 227C, of second skin interfacing surface 227, can apply a stabilizing force 229 in a direction generally normal to the second skin interfacing surface planar region 227C. Together, the stabilizing forces 228, 229 imparted on the skin surface via the first and second skin interfacing surface planar regions 226C, 227C can help to prevent the skin surface, and thus the implant underneath this skin surface, from moving downward (e.g., prevented from moving away from extraction member 230 and toward the skin surface interfacing side 206). This stabilization can be further enhanced in certain examples where the first and second skin interfacing surfaces 226, 227 are close together, and some cases contact one another, at the respective lower portions of the first and second skin interfacing surface planar regions 226C, 227C. Furthermore, the presence of the extraction member 230 can help to prevent the skin surface, and thus the end of the implant underneath this skin surface, from moving back (e.g., toward the extraction member 230 and the end of the device 200 opposite the arms 220, 225).

Accordingly, the skin surface, and thus the implant underneath this skin surface, can be stabilized and its movement impeded in three directions—back (e.g., impeded from moving toward the extraction member 203 and end of the device 200 opposite the arms 220, 225), down at one side (e.g., impeded from moving away from extraction member 230 and toward the skin surface interfacing side 206 at the first arm 220 side), and down at another (e.g., opposite) side (e.g., impeded from moving away from extraction member 230 and toward the skin surface interfacing side 206 at the second arm 225 side). As such, this configuration can resolve forces imparted at the skin surface, and thus at the implant underneath this skin surface, such that the implant has the forward directional degree of movement substantially unimpeded (e.g., substantially unimpeded to move in a direction of movement opposite to, and away from, the extraction member 230). The resolution of these forces as such via the first and second skin interfacing surfaces 226, 227 and extraction member 230 can thus act to facilitate an efficient and repeatable process for stabilizing and removing the implant.

As also illustrated in the exemplary embodiment, the first arm 220 includes a first end portion 231 and the second arm 225 includes a second end portion 232. The first and second end portions 231, 232 can each be opposite an actuation interface 240 of the device 200. The first end portion 231 can have a first width 233, defined in a direction normal to the first arm longitudinal axis 223, that increases in a direction moving along the first arm longitudinal axis 22 toward the actuation interface 240. Likewise, the second end portion 232 can have a second width 234, defined in a direction normal to the second arm longitudinal axis 224, that increases in a direction moving along the second arm longitudinal axis 224 toward the actuation interface 240. As one such example, shown here, each of the first end portion 231 and the second end portion 232 is wedge-shaped. This reduced width 233, 234 at the inlet to the space between the arms 220, 225 can help to prevent the arms 220, 225 from prodding at the skin surface and induce the skin surface inward to the space defined between the arms 220, 225 and, thereby, further help to position the implant underneath this skin surface between the arms 220, 225 and in-line with the extraction member 230.

The implant removal device 200 further includes an extraction member 230 supported at the body 205. As illustrated, the extraction member 230 can be located between the first arm 220 and the second arm 225. In particular, the extraction member 230 can be located between the first arm 220 and the second arm 225 when the first and second arms 220, 225 are in the skin gripping position 221. The extraction member 230 can be configured to engage a skin surface at an end portion of the implant, which end portion extends between the first side of the implant and the second side of the implant, when the first and second arms 220, 225 are in the skin gripping position 221. Similarly, the extraction member 230 can be located between the first arm 220 and the second arm 225 when the first and second arms 220, 225 are in the retracted position 222.

In the illustrated embodiment of the implant removal device 200, the extraction member 230 can be fixed in place at the body 205. In this embodiment, the extraction member 230 can be configured to engage a skin surface at an end portion of the implant and the implant can be moved, using the extraction member 230, by moving the implant removal device 200, including the extraction member 230 fixed at the body 205, along, and relative to, the skin surface so as to cause the implant to move relative to the skin surface.

The extraction member 230 can be located at the body 205 such that the arms 220, 225 extend out from the body 205 beyond the extraction member 233. Also, the extraction member 230 can be located at the body 205 so as to extend to an elevation (e.g., in a direction opposite the skin surface interfacing side 206) above the arms 220, 225. This position of the extraction member 230, relative to the arms 220, 225, can help to facilitate extraction member 230 engagement at the skin surface adjacent the end portion of the implant which, as described further below, can help to move the implant, via the extraction member 203, relative to the skin surface and out through an incision at the skin surface. As also illustrated, and best seen in FIG. 10, the extraction member 230 can include a cross-sectional area 236 that decreases in a direction moving toward the skin surface interfacing side 206 and the arms 220, 225. In this way, the cross-sectional area 236 of the extraction member 230 can be complementary to the configuration of the first and second skin interfacing surfaces 226, 227. In other words, since, in the illustrated embodiment, the first and second skin interfacing surfaces 226, 227 are configured to reduce the space therebetween moving in the direction toward the skin surface interfacing side 206, the cross-sectional area 236 of the extraction member likewise reduces (e.g., in a corresponding manner) at this same location.

The implant removal device 200 additionally includes an actuation interface 240 supported at the body 205. The actuation interface 240 is configured to receive a first actuation input thereat to cause at least one of the first arm 220 and the second arm 225 to move from the skin gripping position 221 to the retracted position 224. Namely, in the illustrated embodiment, the body 205 can be configured to impart a biasing force on each of the first arm 220 and the second arm 225 to bias each of the first and second arms 220, 225 to the skin gripping position 221. And, the body 205 can be configured such that this biasing force is overcome by application of the first actuation input at the actuation interface 240 to cause each of the first and second arm 220, 225 to move from the skin gripping position 221 to the retracted position 222. Additionally, the body 205 can be configured such that, upon removal of the first actuation input at the actuation interface 240, the biasing force acts to move each of the first and second arms 220, 225 from the retracted position 222 to the skin gripping position 221.

In the illustrated example, the actuation interface 240 includes a first handle 241 and a second handle 242 each supported at the body 205. The first handle 241 can be configured to receive the first actuation input thereat to cause the first arm 220 to move from the skin gripping position 221 to the retracted position 222. In particular, the first actuation input can be applied at the first handle 241 in a direction 243 to cause the first handle 241 to move in the direction 243 and, as a result of applying the first actuation input at the first handle 241 in the direction 243, move the first arm 220 from the skin gripping position 221 toward the retracted position 222. And, likewise, the second handle 242 can be configured to receive the first actuation input thereat to cause the second arm 225 to move from the skin gripping position 221 to the retracted position 222. In particular, the first actuation input can be applied at the second handle 242 in a direction 244 to cause the second handle 242 to move in the direction 244 and, as a result of applying the first actuation input at the second handle 242 in the direction 244, move the second arm 225 from the skin gripping position 221 toward the retracted position 222. Then, due to the bias force on the first and second arms 220, 225, when the first actuation input is removed from the first and second handles 241, 242 the first and second arms 220, 225 are urged by this biasing force from the retracted position 222 back to the skin gripping position 221.

As noted, the body 205 can be configured to impart a biasing force on each of the first arm 220 and the second arm 225 to bias each of the first and second arms 220, 225 to the skin gripping position 221. The provide this biasing force, the body 205 can include a biasing member 245 that is configured to impart a biasing force on each of the first arm 220 and the second arm 225 to bias each of the first and second arm 220, 225 to the skin gripping position 221. In the illustrated embodiment, the first and second handles 241, 242 are supported at the body 205 at the biasing member 245. Specifically, the first handle 241 is supported at a first side of the biasing member 245, and the second handle 242 is supported at a second, opposite side of the biasing member 245. In this way, the first and second handles 241, 242 can act to transfer the force from the first actuation input applied at the first and second handles 214, 242 to the biasing member 245 and, as a result, overcome the biasing force imparted by the biasing member 245 and cause the arms 220, 225 to move toward the retracted position 222.

As one example, the biasing member 245 in the illustrated embodiment is in the form of a C-shaped element. The use of a C-shaped element as the biasing member 245 can help to distribute stresses and strains within the body 205 and, resultingly, allow the device 200 to be a smaller device while also providing appropriate structural stability. This C-shaped element can have a first C-shaped end 246 and a second C-shaped end 247 opposite the first C-shaped end 246. As shown, the first handle 241 can be supported at the first C-shaped end 246, and the second handle 242 is supported at the second C-shaped end 247. The extraction member 230 can also be supported at the body 205 at the C-shaped ends 246, 247. Notably, by supporting the handles 241, 242 at the more linear C-shaped ends 246, 247, the amount of force needed from the first actuation input to overcome the biasing force imparted by the biasing member 245 (e.g., C-shaped element) move the arms 220, 225 can be reduced and, thereby, increase user convenience associated with operation of the device 200. Also, by supporting the handles 241, 242 at the more linear C-shaped ends 246, 247, the biasing force imparted by the biasing member 245 (e.g., C-shaped element) can more readily act to bring the arms 220, 225 back to the skin gripping position 221.

Thus, in operation, the device 200 can be configured to facilitate removal of a subdermal implant upon actuation of the actuation interface 240 (e.g., actuation of one or both of handles 241, 242). FIGS. 11-13 show the implant removal device 200 positioned at the skin surface having an implant (e.g., a subdermal implant) 250.

FIG. 11 is a perspective view of the implant removal device 200 positioned at a skin surface 251 that includes the implant 250 underneath the skin surface 251. The implant 250 has a first lateral implant side 252, a second lateral implant side 253 that is opposite the first side 252, and an implant end portion 254 that extends between the first side 252 and the second side 253.

In positioning the implant removal device 200 at the skin surface 251, the first actuation input can be applied at the actuation interface 240 to cause the arms 220, 225 to move toward the retracted position 222. While continuing to apply the first actuation input, and thus while keeping the arms 220, 225 at the retracted position, the device 200 can be placed into contact with the skin surface at the skin surface interfacing side 206 and with the implant 250 positioned between the arms 220, 225. Once the device is positioned as such, the first actuation input can be removed from the actuation interface 240 such that the arms 220, 225 move to the skin gripping position 221. As the first arm 220 is moved from the retracted position 222 to the skin gripping position 221, the first arm 220 can be configured to contact and raise the skin surface 251 at the first side 252 of the implant 250. Likewise, as the second arm 25 is moved from the retracted position 222 to the skin gripping position 221, the second arm 225 can be configured to contact and raise the skin surface 251 at the second side 253 of the implant 250. Raising the skin surface 251 as such can result in raising the implant 250 between the arms 220, 225. Because the extraction member 230 is located between the arms 220, 225 when the arms 220, 225 are in the skin gripping position 221, and the extraction member 230 can be configured to align with the end portion 254 of the implant 250 when the arms 220, 225 are in the skin gripping position 221. As the skin surface 251, and thus the implant 250, is raised by the first and second skin interfacing surfaces 226, 227, the elevation of the extraction member 230, at least in part above the first and second skin interfacing surfaces 226, 227, can further act to align the extraction member 230 with the raised skin surface 251 and raised underlying implant 250.

FIG. 12 is a close-up perspective view of the implant removal device 200 with the first and second arms 220, 225 held by a hand 260 of a user. This can be useful in helping to maintain a secure fit of the arms 220, 225 adjacent the implant 250. As shown here, the hand 260 of the user can be placed at each of the first end portion 231 of the first arm 220 and the second end portion 232 of the second arm 225. The hand 260 of the user can apply one securement force at the first arm 220 in a direction toward the second arm 225, and the hand 260 of the user can apply another securement force at the second arm 225 in a direction toward the first arm 220.

FIG. 13 is a close-up perspective view of the implant removal device 200 with the extraction member 230 moved into engagement with the skin surface 251 adjacent the end portion 254 of the implant 250. For example, when the device 200 is positioned at the skin surface 251 as described (e.g., with the skin surface 251 and underlying implant 250 raised), a user can apply a second actuation force in a direction 261 at the device 200 to move the extraction member 230 into engagement with the skin surface 251 adjacent the end portion 254 of the implant 250. In the illustrated embodiment of the device 200, the extraction member 230 can be fixed relative to the body 205. As such, to move the extraction member 230 into engagement with the skin surface 251 adjacent the end portion 254, the second actuation input in the direction 261 can be provided by the user to translate the device 200 along, and relative to, the skin surface 251 in a direction (e.g., the direction 261) toward the end portion 254. This second actuation input in the direction 261 by the user can thus bring the extraction member 230 into engagement with the skin surface 251 adjacent the end portion 254, such as shown in FIG. 13. Once the extraction member 230 is engaged as such, the second actuation input can continue to be applied in the direction 261, and thereby translate the device 200 along the skin surface 251 in the direction 261, by the user to urge the implant 250, via the extraction member 230, toward an incision 265 created at the skin surface 251. As this second actuation input is continued to be applied in the direction 261, and resultingly the device 200 continues to translate along, and relative to, the skin surface 251 in the direction 261, the extraction member 230 can move the end portion 254 of the implant 250 in the direction 261 such that an end portion 255 of the implant 250 opposite the end portion 254 can begin to exit out from the skin surface 251 via the incision 265. The second actuation input can continue to be applied in the direction 261 until the extraction member 230 has urged enough the of the implant 250 out through the incision 265 that the implant 250 can be grasped (e.g., by a surgical forceps) external to the skin surface 251 and removed from the patient's body.

Notably, the device 200 can be configured in operation, as described, to leverage the natural surface tension present at the skin surface 251. For example, the previously described geometry of the first and second skin interfacing surfaces 226, 227 of the respective arms 200, 225 can be useful in operation in retaining and supporting the implant 250 at the elevated location between the arms 220, 225 while at the same time allowing for the natural surface tension present at the skin surface to draw excess skin at the skin surface out through and under the arms 220, 225 so as to provide a more stabilized retention of the implant 250 between the arms 220, 225.

Also notably, the device 200 can allow for the incision 265 to be made in a more efficient and precise manner. Namely, the device 200 can work in operation such that the device 200 can be used to locate and retain the implant between the arms 220, 225 before creating the incision 265 at the skin surface 251. By allowing for the incision 265 to be made once the location of the implant 250 has been ascertained and the implant 250 has stabilized in position between the arms 220, 225, the size of the incision 265 can be minimized and, as a result, patient discomfort, wound closure effort and resources, and recovery time associated with the implant removal procedure can each be reduced.

Figure 14:
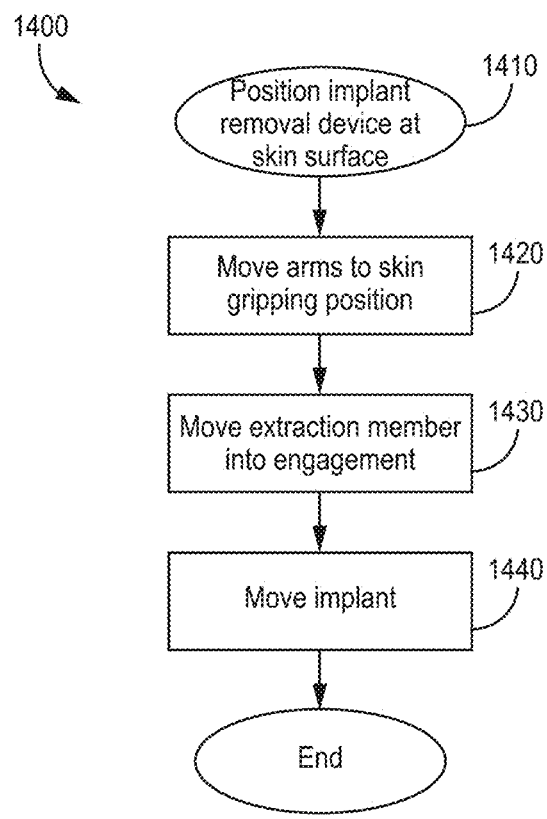
FIG. 14 is a flow diagram of another embodiment of a method of removing an implant (e.g., a subdermal implant).

FIG. 14 is a flow diagram of an embodiment of a method 1400. The method 1400 can be used, for instance, to remove an implant, such as a subdermal implant. The method 1400 can be performed using an implant removal device having one or more of the features (e.g., each of the features) disclosed herein. For example, the method 1400 can be performed using the implant removal device 200.

At step 1410, the method 1400 includes the step of positioning an implant removal device (e.g., the implant removal device 200, the implant removal device 100) at a skin surface. The implant removal device can be positioned at the skin surface, at step 1410, with each of a first arm and a second arm of the implant removal device in a retracted position and with each of the first arm and the second arm on opposite sides (e.g., lateral sides) of the implant.

At step 1420, the method 1400 includes the step of moving each of the first arm and the second arm of the implant removal device from the retracted position to a skin gripping position. When moved to the skin gripping position, the first arm can be adjacent a first side (e.g., a first lateral side) of an implant and the second arm can be adjacent a second side (e.g., a second lateral side) of the implant that is opposite the first side. The first arm and the second arm can be closer together in the skin gripping position than in the retracted position. In addition, in some cases, moving the first arm from the retracted position to the skin gripping position can include contacting the skin surface at the first side of the implant with a first skin interfacing surface of the first arm and raising the skin surface at the first side of the implant. Likewise, in some cases, moving the second arm from the retracted position to the skin gripping position can include contacting the skin surface at the second side of the implant with a second skin interfacing surface of the second arm and raising the skin surface at the second side of the implant. In many such cases, raising the skin surface at the first side of the implant and raising the skin surface at the second side of the implant includes raising the implant.

At step 1430, the method 1400 includes moving an extraction member of the implant removal device into engagement with the skin surface adjacent the implant. This can include moving the extraction member into engagement with the skin surface adjacent the end portion of the implant extending between the first lateral side of the implant and the second lateral side of the implant. The extraction member of the implant removal device can be located between the first arm and the second arm.

At step 1440, the method 1400 can include moving the implant, using the extraction member, relative to the skin surface. This can include bringing the extraction member into contact with the skin surface adjacent the end portion of the implant and moving the extraction member relative to the skin surface so as to thereby move the implant underneath the skin surface. In some embodiments, the extraction member can be fixed in place at the implant removal device, so moving the implant using the extraction member an include moving the implant removal device along, and relative to, the skin surface in order to move the extraction member. Thus, in such embodiments where the extraction member is fixed in place, the implant is moved, using the extraction member, by moving the implant removal device, including the extraction member, along, and relative to, the skin surface so as to cause the implant to move relative to the skin surface.

In some embodiments, the method 1400 can additionally include the step of creating an incision at the skin surface. The step of creating the incision at the skin surface can occur after moving each of the first arm and the second arm to the skin gripping position at the skin surface. This can be useful since the precise location of the implant will have been ascertained and the implant will be stabilized at that location via the first and second arms at the skin gripping position and, as such, can allow the size of the incision to be minimized. In some such cases, the incision can be created at the skin surface opposite the extraction member. This can allow the extraction member to urge the implant out through the incision at an end of the implant opposite where the extraction member is engaged at the skin surface.

Also, in some examples of the method 1400, the extraction member can be moved into contact with the skin surface adjacent the end portion of the implant after moving each of the first arm and the second arm to the skin gripping position. Then implant can be moved, using the extraction member, relative to the skin surface and toward the incision.

Various non-limiting exemplary embodiments have been described. It will be appreciated that suitable alternatives are possible without departing from the scope of the examples described herein.

What is claimed is:

1. A method comprising the steps of:
   positioning an implant removal device at a skin surface with each of a first arm and a second arm of the implant removal device in a retracted position;
   moving each of the first arm and the second arm of the implant removal device from the retracted position to a skin gripping position such that the first arm is adjacent a first side of an implant and the second arm is adjacent a second side of the implant, the second side being opposite the first side, the first arm and the second arm being closer together in the skin gripping position than in the retracted position;
   moving an extraction member of the implant removal device into engagement with the skin surface adjacent an end portion of the implant, the end portion of the implant extending between the first side of the implant and the second side of the implant, the extraction member being located between the first arm and the second arm; and
   moving the implant, using the extraction member, relative to the skin surface.

2. The method of claim 1, further comprising the step of:
   after moving each of the first arm and the second arm to the skin gripping position at the skin surface, creating an incision at the skin surface.

3. The method of claim 2, wherein the incision is created at the skin surface opposite the extraction member.

4. The method of claim 2,
   wherein the extraction member is moved into contact with the skin surface adjacent the end portion of the implant after moving each of the first arm and the second arm to the skin gripping position, and
   wherein the implant is moved, using the extraction member, relative to the skin surface and toward the incision.

5. The method of claim 1, further comprising the steps of:
   when moving the first arm from the retracted position to the skin gripping position, contacting the skin surface at the first side of the implant with a first skin interfacing surface of the first arm and raising the skin surface at the first side of the implant; and
   when moving the second arm from the retracted position to the skin gripping position, contacting the skin surface at the second side of the implant with a second skin interfacing surface of the second arm and raising the skin surface at the second side of the implant.

6. The method of claim 5, wherein raising the skin surface at the first side of the implant and raising the skin surface at the second side of the implant includes raising the implant.

7. The method of claim 1, wherein the implant is moved, using the extraction member, by moving the implant removal device, including the extraction member, along, and relative to, the skin surface so as to cause the implant to move relative to the skin surface.

8. A method comprising the steps of:
- positioning an implant removal device at a skin surface with at least one of a first arm and a second arm of the implant removal device in a retracted position;
- moving the at least one of the first arm and the second arm of the implant removal device from the retracted position to a skin gripping position such that the first arm is adjacent a first side of an implant and the second arm is adjacent a second side of the implant, the second side being opposite the first side, the first arm and the second arm being closer together in the skin gripping position than in the retracted position;
- bringing an extraction member of the implant removal device into engagement with the skin surface adjacent a first end portion of the implant, the first end portion of the implant extending between the first side of the implant and the second side of the implant, the extraction member being located between the first arm and the second arm;
- creating an incision at the skin surface near a second end portion of the implant, the second end portion of the implant being opposite the first end portion of the implant; and
- moving the implant removal device along the skin surface with the extraction member in contact with the skin surface adjacent the first end portion of the implant so that as the implant removal device is moved along the skin surface the extraction member acts to move the implant toward the incision at the skin surface near the second end portion of the implant.

9. The method of claim 8, wherein as the implant removal device is moved along the skin surface the extraction member acts to move the implant underneath the skin surface and toward the incision at the skin surface near the second end portion of the implant.

10. The method of claim 8, wherein the implant removal device is moved along the skin surface with the extraction member in contact with the skin surface adjacent the first end portion of the implant while the first arm and the second arm are in the skin gripping position.

11. The method of claim 8, wherein moving the at least one of the first arm and the second arm of the implant removal device from the retracted position to the skin gripping position comprises moving each of the first arm and the second arm of the implant removal device from the retracted position to the skin gripping position.

12. The method of claim 11, further comprising the steps of:
- when moving the first arm from the retracted position to the skin gripping position, contacting the skin surface at the first side of the implant with a first skin interfacing surface of the first arm and raising the skin surface at the first side of the implant; and
- when moving the second arm from the retracted position to the skin gripping position, contacting the skin surface at the second side of the implant with a second skin interfacing surface of the second arm and raising the skin surface at the second side of the implant.

13. The method of claim 11, wherein the incision is created at the skin surface near the second end portion of the implant after each of the first arm and the second arm of the implant removal device are moved from the retracted position to the skin gripping position.

14. The method of claim 13, wherein the extraction member is brought into engagement with the skin surface adjacent the first end portion of the implant while the first arm and the second arm are in the skin gripping position.

15. The method of claim 8, wherein the incision is created at the skin surface at one location at the skin surface opposite another location at the skin surface at which the extraction member is brought into contact with the skin surface that is adjacent the first end portion of the implant.

16. The method of claim 8, wherein the extraction member is fixed in place at the implant removal device such that moving the implant removal device along the skin surface moves the extraction member along the skin surface.

17. The method of claim 8, wherein the extraction member is brought into engagement with the skin surface adjacent the first end portion of the implant before moving the at least one of the first arm and the second arm from the retracted position to the skin gripping position.

18. The method of claim 8, wherein moving the implant removal device along the skin surface with the extraction member in contact with the skin surface adjacent the first end portion of the implant comprises a user pushing on the body of the implant removal device in a direction parallel to a longitudinal axis of the implant and toward the incision at the skin surface.

19. A method comprising the steps of:
- positioning an implant removal device at a skin surface with at least one of a first arm and a second arm of the implant removal device in a retracted position;
- moving the at least one of the first arm and the second arm of the implant removal device from the retracted position to a skin gripping position such that the first arm is adjacent a first side of an implant and the second arm is adjacent a second side of the implant, the second side being opposite the first side, the first arm and the second arm being closer together in the skin gripping position than in the retracted position;
- bringing an extraction member of the implant removal device into engagement with the skin surface adjacent a first end portion of the implant, the first end portion of the implant extending between the first side of the implant and the second side of the implant, the extraction member being located between the first arm and the second arm;
- creating an incision at the skin surface near a second end portion of the implant, the second end portion of the implant being opposite the first end portion of the implant; and
- moving the implant removal device along the skin surface with the extraction member in contact with the skin surface adjacent the first end portion of the implant so that as the implant removal device is moved along and in contact with the skin surface the extraction member acts to move the implant underneath the skin surface and toward the incision at the skin surface near the second end portion of the implant.

20. The method of claim 19, wherein the incision is created at the skin surface at one location at the skin surface opposite another location at the skin surface at which the extraction member is brought into contact with the skin surface that is adjacent the first end portion of the implant.

* * * * *